(12) United States Patent
de Fougerolles et al.

(10) Patent No.: US 11,149,273 B2
(45) Date of Patent: Oct. 19, 2021

(54) LIPID FORMULATED COMPOSITIONS AND METHODS FOR INHIBITING EXPRESSION OF SERUM AMYLOID A GENE

(71) Applicant: Alnylam Pharmaceuticals, Inc., Cambridge, MA (US)

(72) Inventors: Antonin de Fougerolles, Brookline, MA (US); Tatiana Novobrantseva, Wellesley, MA (US); Gregory Hinkle, Plymouth, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 16/592,644

(22) Filed: Oct. 3, 2019

(65) Prior Publication Data

US 2020/0239887 A1    Jul. 30, 2020

Related U.S. Application Data

(63) Continuation of application No. 15/847,631, filed on Dec. 19, 2017, now Pat. No. 10,472,628, which is a continuation of application No. 14/932,782, filed on Nov. 4, 2015, now Pat. No. 9,868,950, which is a continuation of application No. 14/012,909, filed on Aug. 28, 2013, now Pat. No. 9,206,421, which is a continuation of application No. 13/120,301, filed as application No. PCT/US2009/058480 on Sep. 25, 2009, now Pat. No. 8,546,554.

(60) Provisional application No. 61/100,195, filed on Sep. 25, 2008.

(51) Int. Cl.
| | |
|---|---|
| C07H 21/02 | (2006.01) |
| C07H 21/04 | (2006.01) |
| C12N 15/113 | (2010.01) |
| A61K 31/713 | (2006.01) |

(52) U.S. Cl.
CPC .......... *C12N 15/113* (2013.01); *A61K 31/713* (2013.01); *C12N 2310/11* (2013.01); *C12N 2310/14* (2013.01); *C12N 2310/321* (2013.01); *C12N 2310/344* (2013.01); *C12N 2310/3515* (2013.01)

(58) Field of Classification Search
CPC .......... C12N 2310/14; C12N 2310/321; C12N 15/113
See application file for complete search history.

(56) References Cited

U.S. PATENT DOCUMENTS

| | | | |
|---|---|---|---|
| 7,427,605 B2 | 9/2008 | Davis et al. | |
| 7,691,997 B2 | 4/2010 | Khvorova et al. | |
| 7,718,629 B2 | 5/2010 | Bumcrot et al. | |
| 2003/0143732 A1 | 7/2003 | Fosnaugh et al. | |
| 2003/0170891 A1 | 9/2003 | McSwiggen | |
| 2003/0229037 A1 | 12/2003 | Massing et al. | |
| 2004/0259247 A1 | 12/2004 | Tuschl et al. | |
| 2006/0008910 A1 | 1/2006 | MacLachlan et al. | |
| 2006/0083780 A1 | 4/2006 | Heyes et al. | |
| 2006/0240093 A1 | 10/2006 | MacLachlan et al. | |
| 2006/0263435 A1 | 11/2006 | Davis et al. | |
| 2007/0004664 A1 | 1/2007 | McSwiggen et al. | |
| 2007/0031844 A1 | 2/2007 | Khvorova et al. | |
| 2007/0135372 A1 | 6/2007 | MacLachlan et al. | |
| 2007/0281899 A1 | 12/2007 | Bumcrot et al. | |
| 2008/0188675 A1 | 8/2008 | Chen et al. | |
| 2009/0023215 A1 | 1/2009 | Jessee et al. | |
| 2009/0023673 A1 | 1/2009 | Manoharan et al. | |
| 2009/0149403 A1 | 6/2009 | MacLachlan | |
| 2009/0291131 A1 | 11/2009 | Maclachlan et al. | |
| 2010/0130588 A1 | 5/2010 | Yaworski | |
| 2010/0324120 A1 | 12/2010 | Chen et al. | |
| 2011/0015250 A1 | 1/2011 | Bumcrot et al. | |
| 2012/0244207 A1 | 9/2012 | Fitzgerald et al. | |

FOREIGN PATENT DOCUMENTS

| | | |
|---|---|---|
| WO | WO 2004/080406 | 9/2004 |
| WO | WO 2004/090108 | 10/2004 |
| WO | WO 2005/120152 | 12/2005 |
| WO | WO 2006/071691 A2 | 7/2006 |
| WO | WO 2007/012191 | 2/2007 |
| WO | WO 2008/042973 | 4/2008 |
| WO | WO 2009/086558 A1 | 7/2009 |
| WO | WO 2009/127060 | 10/2009 |
| WO | WO 2010/054406 | 5/2010 |
| WO | WO 2010/088537 | 8/2010 |
| WO | WO 2010/129709 | 11/2010 |
| WO | WO 2010/144740 | 12/2010 |
| WO | WO 2010/147992 | 12/2010 |

OTHER PUBLICATIONS

Agrawal, S., et al., "Antisense oligonucleotides: towards clinical trials." Trends in Biotechnology. Oct. 1996, vol. 14, pp. 376-387.
Bass, B., "The short answer," Nature, May 24, 2001, pp. 428-429, vol. 411.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in *Drosophila melanogaster* Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in Caenorhabditis elegans," Nature, Feb. 19, 1998, pp. 806-811, vol. 391.

(Continued)

*Primary Examiner* — Amy H Bowman
(74) *Attorney, Agent, or Firm* — Goodwin Procter LLP

(57) ABSTRACT

The invention relates to a double-stranded ribonucleic acid (dsRNA) targeting a Serum Amyloid A (SAA) gene, and methods of using the dsRNA to inhibit expression of SAA

17 Claims, 10 Drawing Sheets

Specification includes a Sequence Listing.

(56) References Cited

OTHER PUBLICATIONS

Han, C.,Y., et al., "Adipocyte-Derived Serum Amyloid A3 and Hyaluronan Play a Role in Monocyte Recruitment and Adhesion," Diabetes, Sep. 2007, pp. 2230-2273, vol. 56.

Herweijer, H., et al., "Time course of gene expression after plasmid DNA gene transfer to the liver," The Journal of Gene Medicine, 3:3, 2001, p. 280-291.

Hornung, V., et al., "Sequence-specific potent induction of IFN-.alpha. by short interfering RNA in plasmacytoid dendritic cells through TLR7," Nature Medicine, Mar. 2005, pp. 263-270, vol. 11, No. 3.

Judge, A., et al., "Confirming the RNAi-mediated mechanism of action of siRNA-based cancer therapeutics in mice," The Journal of Clinical Investigation, 2009, pp. 1-13.

Love, K., et al., "Lipid-like materials for low-dose, in vivo gene silencing," PNAS, Feb. 2, 2010, pp. 1864-1869, vol. 107, No. 5.

Nguyen, A., et al., "Evaluation of Gene Promoters for Liver Expression by Hydrodynamic Gene Transfer," J. Surg. Res., 148:1, Jul. 2008, p. 60-66.

Office Action for U.S. Appl. No. 13/120,601, dated Nov. 6, 2012, 9 Pages.

PCT International Search Report and Written Opinion, PCT/US2009/058480, dated Dec. 28, 2009, 11 Pages.

Postic, C., et al., "DNA Excision in Liver by an Albumin-Cre Transgene Occurs Progressively with Age," Genesis, Feb. 2000; 26(2):149-150.

Reynolds, et al. (2004) "Rational siRNA design for RNA interference," Nature Biotechnology, vol. 22, No. 3, pp. 326-330.

Robbins, M., et al., "Stable expression of shRNAs in human CD34.sup.+ progenitor cells can avoid induction of interferon responses to siRNAs in vitro," Nature Biotechnology, May 2006, pp. 566-571, vol. 24, No. 5.

Rose, S., et al., "Functional polarity is introduced by Dicer processing of short substrate RNAs," Nucleic Acids Research, 2005, pp. 4140-4156, vol. 33, No. 13.

Tuschl T., "RNA Interference and Small Interfering RNAs" Chembiochem, 2001, pp. 239-245, vol. 2.

Tuschl, T., "Expanding small RNA interference," Nature Biotechnology, May 2002, pp. 446-448, vol. 20.

Tuschl, T., "Functional genomics: RNA sets the standard," Nature, Jan. 16, 2003, vol. 421, No. 6920, pp. 220-221.

Tuschl, T., "Mammalian RNA Interference," RNAi, A Guide to Gene Silencing, Chapter 13, G.J. Hannon (ed,), 2003, pp. 265-295.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., et al., "Targeted mRNA Degradation by Double-Stranded RNA In Vitro," Genes & Development, 1999, pp. 3191-3197, vol. 13.

Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.

Weil, et al (2002) "Targeting the Kinesin Eg5 to Monitor siRNA Transfection in Mammalian Cells," Biotechniques 33(6):1244-1248.

Zimmerman, et al., "RNAi-mediated gene silencing in non-human primates," Nature, May 4, 2006, pp. 111-114, vol. 441, With supplementary information.

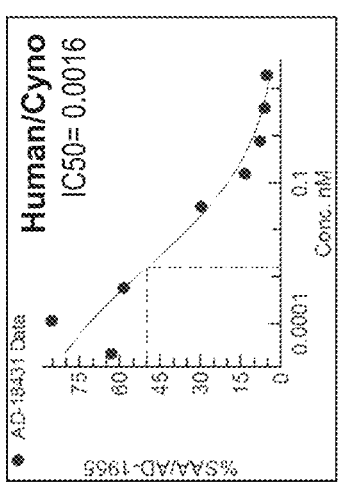
FIG. 4A
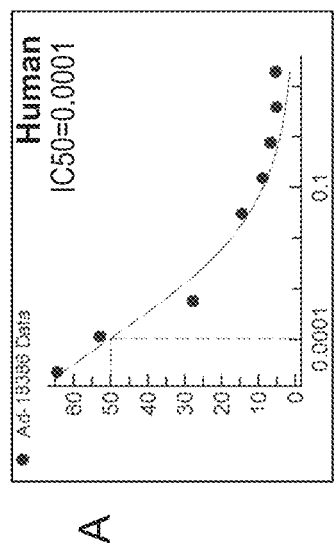
FIG. 4B
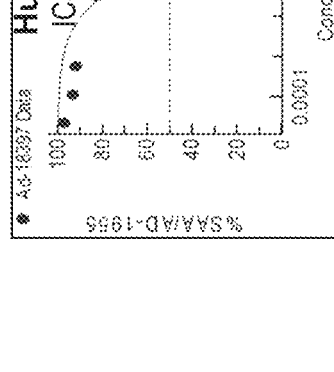
FIG. 4C
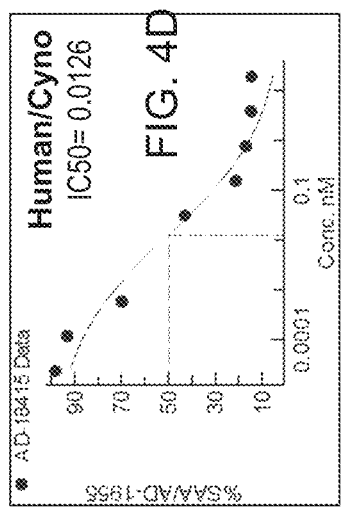
FIG. 4D
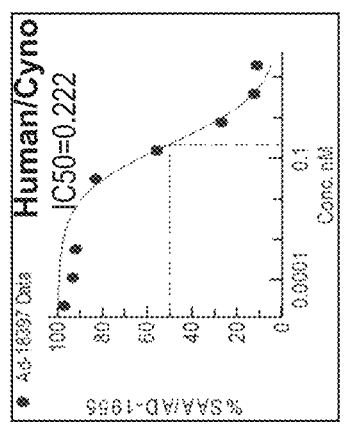
FIG. 4E
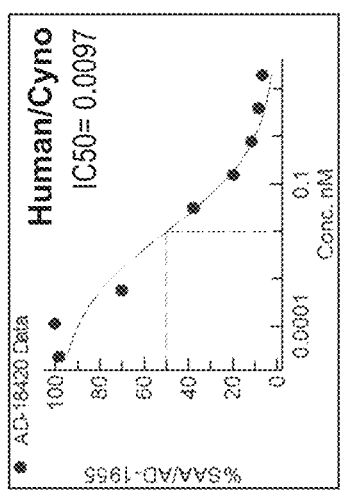
FIG. 4F
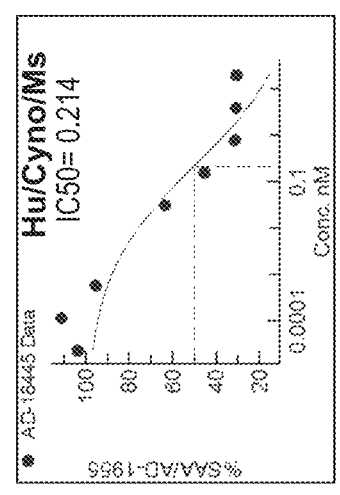
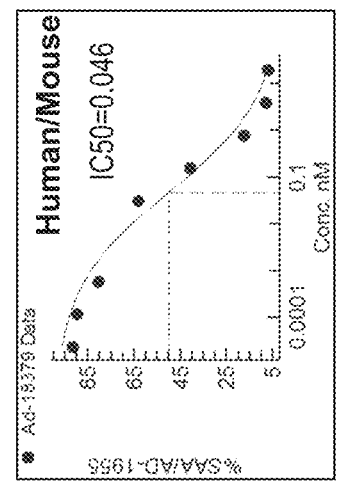
FIG. 4G

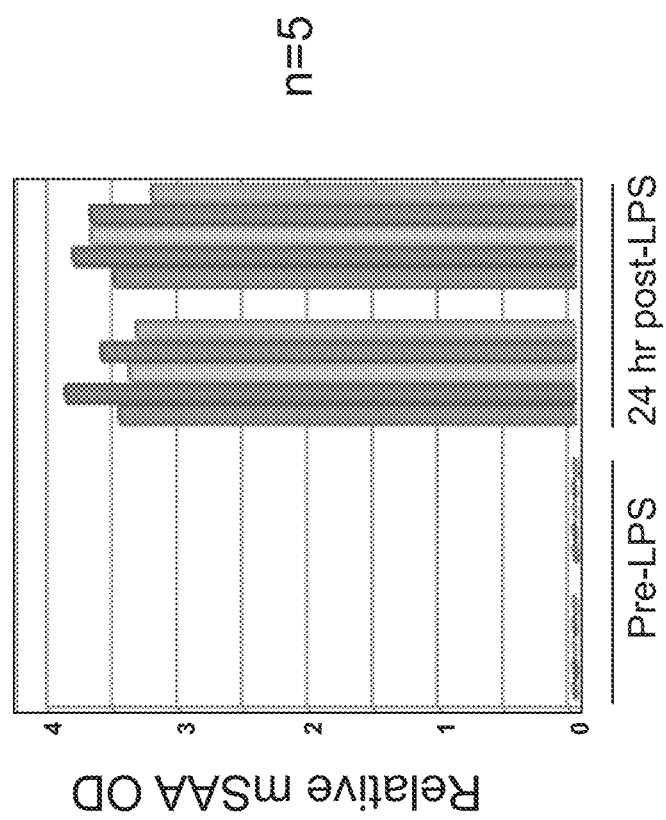

SEQUENCE LISTING

```
<160> NUMBER OF SEQ ID NOS: 318

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
ccaugcucgg gggaacuaut t                                               21
```

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 2
auaguucccc cgagcauggt t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 3
ggcuuuugau ggggcucggt t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 4
ccgagcccca ucaaaagcct t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 5
ucuuuucguu ccuuggcgat t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 6
ucgccaagga acgaaaagat t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
agaagccaau uacaucggct t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
gccgauguaa uuggcuucut t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
ucggcucaga caaauacuut t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
aaguauuugu cugagccgat t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
aauacuucca ugcucggggt t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
ccccgagcau ggaaguauut t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
cccaaucacu uccgaccugt t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
caggucggaa gugauugggt t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
ccgaagcuuc uuuucguuct t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 16
gaacgaaaag aagcuucggt t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
aauuacaucg gcucagacat t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
ugucugagcc gauguaauut t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
uuacaucggc ucagacaaat t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
uuugucugag ccgauguaat t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

-continued

<400> SEQUENCE: 21
uuccaugcuc gggggaacut t                                          21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22 aguuccccg agcauggaat t                                           21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 23
caugcucggg ggaacuaugt t                                          21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 24
cauaguuccc ccgagcaugt t                                          21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 25
gcuuuugaug gggcucgggt t                                          21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic oligonucleotide

<400> SEQUENCE: 26
cccgagcccc aucaaaagct t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
agccuacucu gacaugagat t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28
ucucauguca gaguaggcut t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 29
caucggcuca gacaaauact t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 30
guauuugucu gagccgaugt t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

<223> OTHER INFORMATION: Description of Artificial Sequence: Synthetic
     oligonucleotide

<400> SEQUENCE: 31
agaccccaau cacuuccgat t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
     Synthetic oligonucleotide
<220> FEATURE:
<223> OTHER INFORMATION: Description of Artificial Sequence: Synthetic
     oligonucleotide

<400> SEQUENCE: 32
ucggaaguga uuggguucut t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
     Synthetic oligonucleotide
<220> FEATURE:
<223> OTHER INFORMATION: Description of Artificial Sequence: Synthetic
     oligonucleotide

<400> SEQUENCE: 33
cugagaaaua cugagcuuct t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
     Synthetic oligonucleotide
<220> FEATURE:
<223> OTHER INFORMATION: Description of Artificial Sequence: Synthetic
     oligonucleotide

<400> SEQUENCE: 34
gaagcucagu auuucucagt t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
     Synthetic oligonucleotide
<220> FEATURE:
<223> OTHER INFORMATION: Description of Artificial Sequence: Synthetic
     oligonucleotide

<400> SEQUENCE: 35
agccgaagcu ucuuuucgut t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
     Synthetic oligonucleotide <220> FEATURE:
<223> OTHER INFORMATION: Description of Artificial Sequence: Synthetic
      oligonucleotide

<400> SEQUENCE: 36
acgaaaagaa gcuucggcut t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 37 cuuucguuc cuuggcgagt t                                               21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 38
cucgccaagg aacgaaaagt t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 39
uuuucguucc uuggcgaggt t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 40
ccucgccaag gaacgaaaat t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:

Synthetic oligonucleotide
<220> FEATURE:
<223> OTHER INFORMATION: Description of Artificial Sequence: Synthetic
      oligonucleotide

<400> SEQUENCE: 41
ccaauuacau cggcucagat t                                                   21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 42
ucugagccga uguaauuggt t                                                   21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 43
caauuacauc ggcucagact t                                                   21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 44
gucugagccg auguaauugt t                                                   21

<210> SEQ ID NO 45
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 45
ggcgaggcuu uugaugpggt t                                                   21

<210> SEQ ID NO 46
<211> LENGTH: 21
<212> TYPE: DNA
<213> ORGANISM: Artificial Sequence
<220> FEATURE:

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 46
ccccaucaaa agccucgcct t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 47
ggcucgggac auguggagat t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 48
ucuccacaug ucccgagcct t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 49
acaugagaga agccaauuat t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 50
uaauuggcuu cucucaugut t                                              21

<210> SEQ ID NO 51
<211> LENGTH: 21
<212> TYPE: DNA
<213> ORGANISM: Artificial Sequence
```

-continued

<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 51
caugagagaa gccaauuact t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 52
guaauuggcu cucucaugt t                                               21

<210> SEQ ID NO 53
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 53
agccaauuac aucggcucat t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 54
ugagccgaug uaauuggcut t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 55
gccaauuaca ucggcucagt t                                              21

<210> SEQ ID NO 56
<211> LENGTH: 21
<212> TYPE: DNA

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 56
cugagccgau guaauuggct t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 57
cggcucagac aaauacuuct t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 58
gaaguauuug ucugagccgt t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 59
caugaagcuu cucacgggct t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 60
gcccgugaga agcuucaugt t                                              21

<210> SEQ ID NO 61
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 61
ggccauggug cggaggacut t                                             21

<210> SEQ ID NO 62
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 62
aguccuccgc accauggcct t                                             21

<210> SEQ ID NO 63
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 63
gaccccaauc acuuccgact t                                             21

<210> SEQ ID NO 64
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 64
gucggaagug auuggguct t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 65
ccccaaucac uuccgaccut t                                             21

<210> SEQ ID NO 66
```

-continued

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 66
aggucggaag ugauuggggt t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 67
gccugccuga gaaauacugt t                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 68
caguauuucu caggcaggct t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 69
gccgaagcuu cuuuucguut t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 70
aacgaaaaga agcuucggct t                                              21
```

```
<210> SEQ ID NO 71
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 71
gaagcuucuu uucguuccut t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 72
aggaacgaaa agaagcuuct t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 73
aagcuucuuu ucguuccuut t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 74
aaggaacgaa aagaagcuut t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 75
cguuccuugg cgaggcuuut t                                              21
```

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 76
aaagccucgc caaggaacgt t                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 77
guuccuuggc gaggcuuuut t                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 78
aaaagccucg ccaaggaact t                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 79
cuuggcgagg cuuuugaugt t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 80
caucaaaagc cucgccaagt t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 81
uggcgaggcu uuugaugggt t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 82
cccaucaaaa gccucgccat t                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 83
cucugacaug agagaagcct t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 84
ggcuucucuc augucagagt t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 85
cacgggccug guuuucugct t                                          21

<210> SEQ ID NO 86
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 86
gcagaaaacc aggcccgugt t                                          21

<210> SEQ ID NO 87
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 87
cuuuugaugg ggcucgggat t                                          21

<210> SEQ ID NO 88
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 88
ucccgagccc caucaaaagt t                                          21

<210> SEQ ID NO 89
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 89
uuggcgaggc uuuugauggt t                                          21

<210> SEQ ID NO 90
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 90
ccaucaaaag ccucgccaat t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 91
acuuccaugc ucggggaat t                                               21

<210> SEQ ID NO 92
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 92 uuccccgag cauggaagut t                                               21

<210> SEQ ID NO 93
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 93
uuuucugcuc cuugguccut t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 94
aggaccaagg agcagaaaat t                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 95
cuucucacgg gccugguuut t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 96
aaaccaggcc cgugagaagt t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 97
auuacaucgg cucagacaat t                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 98
uugucugagc cgauguaaut t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 99
auacuuccau gcucgggggt t                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

<400> SEQUENCE: 100
cccccgagca uggaaguaut t                                               21

<210> SEQ ID NO 101
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 101
gcgaggcuuu ugaugggct t                                                21

<210> SEQ ID NO 102
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 102
gccccaucaa aagccucgct t                                               21

<210> SEQ ID NO 103
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 103
gcucgggaca uguggagagt t                                               21

<210> SEQ ID NO 104
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 104
cucuccacau gucccgagct t                                               21

<210> SEQ ID NO 105
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic -continued oligonucleotide

<400> SEQUENCE: 105
acauguggag agccuacuct t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 106
gaguaggcuc uccacaugut t                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 107
uccaugcucg ggggaacuat t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 108 uaguucccc gagcauggat t                                               21

<210> SEQ ID NO 109
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 109
aucacuuccg accugcuggt t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

<223> OTHER INFORMATION: Description of Artificial Sequence: Synthetic
      oligonucleotide

<400> SEQUENCE: 110
ccagcagguc ggaagugaut t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 111
ggacaugugg agagccuact t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 112
guaggcucuc cacaugucct t                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 113
cauguggaga gccuacucut t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 114
agaguaggcu cuccacaugt t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide

```
<220> FEATURE:
<223> OTHER INFORMATION: Description of Artificial Sequence: Synthetic
      oligonucleotide

<400> SEQUENCE: 115
ggagagccua cucugacaut t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 116
augucagagu aggcucucct t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 117
gagagccuac ucugacaugt t                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 118
caugucagag uaggcucuct t                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 119
uacucugaca ugagagaagt t                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Combined DNA/RNA Molecule:
```

Synthetic oligonucleotide
<220> FEATURE:
<223> OTHER INFORMATION: Description of Artificial Sequence: Synthetic
      oligonucleotide

<400> SEQUENCE: 120
cuucucucau gucagaguat t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 121
gaagccaauu acaucggcut t                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 122
agccgaugua auuggcuuct t                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 123
gcucagacaa auacuuccat t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 124
uggaaguauu ugucugagct t                                              21

<210> SEQ ID NO 125
<211> LENGTH: 21
<212> TYPE: DNA
<213> ORGANISM: Artificial Sequence
<220> FEATURE:

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 125
uacuuccaug cucgggggat t                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 126 uccccccgagc auggaaguat t                                             21

<210> SEQ ID NO 127
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 127
caccaugaag cuucucacgt t                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 128
cgugagaagc uucauggugt t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 129
gccaaaaggg gaccuggggt t                                              21

<210> SEQ ID NO 130
<211> LENGTH: 21
<212> TYPE: DNA
<213> ORGANISM: Artificial Sequence
```

<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 130
ccccaggucc ccuuuuggct t                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 131
augaagcuuc ucacgggcct t                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 132
ggcccgugag aagcuucaut t                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 133
gccauggugc ggaggacuct t                                              21

<210> SEQ ID NO 134
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 134
gaguccuccg caccauggct t                                              21

<210> SEQ ID NO 135
<211> LENGTH: 21
<212> TYPE: DNA

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 135
ccauggugcg gaggacucgt t                                               21

<210> SEQ ID NO 136
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 136
cgaguccucc gcaccauggt t                                               21

<210> SEQ ID NO 137
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 137
cgggccuggu uuucugcuct t                                               21

<210> SEQ ID NO 138
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 138
gagcagaaaa ccaggcccgt t                                               21

<210> SEQ ID NO 139
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 139
ugucagcagc cgaagcuuct t                                               21

<210> SEQ ID NO 140
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 140
gaagcuucgg cugcugacat t                                              21

<210> SEQ ID NO 141
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 141
gcagccgaag cuucuuuuct t                                              21

<210> SEQ ID NO 142
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 142
gaaaagaagc uucggcugct t                                              21

<210> SEQ ID NO 143
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 143
gcuucuuuuc guccuuggt t                                               21

<210> SEQ ID NO 144
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 144
ccaaggaacg aaaagaagct t                                              21

<210> SEQ ID NO 145
```

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 145
uuccuuggcg aggcuuuugt t                                              21

<210> SEQ ID NO 146
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 146
caaaagccuc gccaaggaat t                                              21

<210> SEQ ID NO 147
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 147
uccuuggcga ggcuuuugat t                                              21

<210> SEQ ID NO 148
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 148
ucaaaagccu cgccaaggat t                                              21

<210> SEQ ID NO 149
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 149
gaaauacuga gcuuccucut t                                              21
```

```
<210> SEQ ID NO 150
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 150
agaggaagcu caguauuuct t                                              21

<210> SEQ ID NO 151
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 151
accccaauca cuuccgacct t                                              21

<210> SEQ ID NO 152
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 152
ggucggaagu gauuggggut t                                              21

<210> SEQ ID NO 153
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 153
gggggaacua ugaugcugct t                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 154
gcagcaucau aguuccccct t                                              21
```

<210> SEQ ID NO 155
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 155
agacaaauac uuccaugcut t                                            21

<210> SEQ ID NO 156
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 156
agcauggaag uauuugucut t                                            21

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
ccaugcucgg gggaacuau                                               19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
auaguucccc cgagcaugg                                               19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
ggcuuuugau ggggcucgg                                               19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
ccgagcccca ucaaaagcc                                                    19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
ucuuuucguu ccuuggcga                                                    19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ucgccaagga acgaaaaga                                                    19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
agaagccaau uacaucggc                                                    19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
gccgauguaa uuggcuucu                                                    19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
ucggcucaga caaauacuu                                                    19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 166
aaguauuugu cugagccga                                                19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
aauacuucca ugcucgggg                                                19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ccccgagcau ggaaguauu                                                19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
cccaaucacu uccgaccug                                                19

<210> SEQ ID NO 170
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 170
aggucggaag ugauugggtt                                               20

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ccgaagcuuc uuuucguuc                                                19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 172
gaacgaaaag aagcuucgg                                                19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
aauuacaucg gcucagaca                                                19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ugucugagcc gauguaauu                                                19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uuacaucggc ucagacaaa                                                19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
uuugucugag ccgauguaa                                                19

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uuccaugcuc gggggaacu                                                19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178 aguuccccg agcauggaa                                              19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
caugcucggg ggaacuaug                                             19

<210> SEQ ID NO 180
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
cauaguuccc ccgagcaug                                             19

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
gcuuuugaug gggcucggg                                             19

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
cccgagcccc aucaaaagc                                             19

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
agccuacucu gacaugaga                                             19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 184
ucucauguca gaguaggcu                                                   19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
caucggcuca gacaaauac                                                   19

<210> SEQ ID NO 186
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
guauuugucu gagccgaug                                                   19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
agaccccaau cacuuccga                                                   19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
ucggaaguga uuggggucu                                                   19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
cugagaaaua cugagcuuc                                                   19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
```
gaagcucagu auuucucag                                               19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
agccgaagcu ucuuuucgu                                               19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
acgaaaagaa gcuucggcu                                               19

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
cuuuucguuc cuuggcgag                                               19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
cucgccaagg aacgaaaag                                               19

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
uuuucguucc uuggcgagg                                               19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
ccucgccaag gaacgaaaa                                             19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
ccaauuacau cggcucaga                                             19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
ucugagccga uguaauugg                                             19

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
caauuacauc ggcucagac                                             19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
gucugagccg auguaauug                                             19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
ggcgaggcuu uugaugggg                                             19

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
ccccaucaaa agccucgcc                                             19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
ggcucgggac auguggaga                                               19

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
ucuccacaug ucccgagcc                                               19

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
acaugagaga agccaauua                                               19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
uaauuggcuu cucucaugu                                               19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
caugagagaa gccaauuac                                               19

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
guaauuggcu cucucaug                                                19

```
<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
agccaauuac aucggcuca                                                  19

<210> SEQ ID NO 210
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
ugagccgaug uaauuggcu                                                  19

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
gccaauuaca ucggcucag                                                  19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
cugagccgau guaauuggc                                                  19

<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
cggcucagac aaauacuuc                                                  19

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
gaaguauuug ucugagccg                                                  19
```

```
<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
caugaagcuu cucacgggc                                                   19

<210> SEQ ID NO 216
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
gcccgugaga agcuucaug                                                   19

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
ggccauggug cggaggacu                                                   19

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
aguccuccgc accauggcc                                                   19

<210> SEQ ID NO 219
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
gaccccaauc acuuccgac                                                   19

<210> SEQ ID NO 220
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
gucggaagug auuggggguc                                                  19

<210> SEQ ID NO 221
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
ccccaaucac uuccgaccu                                                       19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
aggucggaag ugauugggg                                                       19

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
gccugccuga gaaauacug                                                       19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
caguauuucu caggcaggc                                                       19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
gccgaagcuu cuuuucguu                                                       19

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
aacgaaaaga agcuucggc                                                       19

<210> SEQ ID NO 227
<211> LENGTH: 19
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
gaagcuucuu uucguuccu                                                    19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
aggaacgaaa agaagcuuc                                                    19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
aagcuucuuu ucguuccuu                                                    19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
aaggaacgaa aagaagcuu                                                    19

<210> SEQ ID NO 231
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
cguuccuugg cgaggcuuu                                                    19

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
aaagccucgc caaggaacg                                                    19

<210> SEQ ID NO 233
<211> LENGTH: 19
<212> TYPE: RNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 233
guuccuuggc gaggcuuuu                                                      19

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
aaaagccucg ccaaggaac                                                      19

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
cuuggcgagg cuuugaug                                                       19

<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
caucaaaagc cucgccaag                                                      19

<210> SEQ ID NO 237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
uggcgaggcu uuugauggg                                                      19

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
cccaucaaaa gccucgcca                                                      19

<210> SEQ ID NO 239
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 239
cucugacaug agagaagcc                                                    19

<210> SEQ ID NO 240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
ggcuucucuc augucagag                                                    19

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
cacgggccug guuucugc                                                     19

<210> SEQ ID NO 242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gcagaaaacc aggcccgug                                                    19

<210> SEQ ID NO 243
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
cuuuugaugg ggcucggga                                                    19

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
ucccgagccc caucaaaag                                                    19

<210> SEQ ID NO 245
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 245
uuggcgaggc uuuugaugg                                                    19

<210> SEQ ID NO 246
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
ccaucaaaag ccucgccaa                                                    19

<210> SEQ ID NO 247
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
acuuccaugc ucgggggaa                                                    19

<210> SEQ ID NO 248
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248 uuccccgag cauggaagu                                                     19

<210> SEQ ID NO 249
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
uuuucugcuc cuugguccu                                                    19

<210> SEQ ID NO 250
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
aggaccaagg agcagaaaa                                                    19

<210> SEQ ID NO 251
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 251
cuucucacgg gccugguuu                                                19

<210> SEQ ID NO 252
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
aaaccaggcc cgugagaag                                                19

<210> SEQ ID NO 253
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
auuacaucgg cucagacaa                                                19

<210> SEQ ID NO 254
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
uugucugagc cgauguaau                                                19

<210> SEQ ID NO 255
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
auacuuccau gcucggggg                                                19

<210> SEQ ID NO 256
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
cccccgagca uggaaguau                                                19

<210> SEQ ID NO 257
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
gcgaggcuuu ugaugggc                                              19

<210> SEQ ID NO 258
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
gccccaucaa aagccucgc                                             19

<210> SEQ ID NO 259
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
gcucgggaca uguggagag                                             19

<210> SEQ ID NO 260
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
cucuccacau gucccgagc                                             19

<210> SEQ ID NO 261
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
acauguggag agccuacuc                                             19

<210> SEQ ID NO 262
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
gaguaggcuc uccacaugu                                             19

<210> SEQ ID NO 263
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 263
uccaugcucg ggggaacua                                                19

<210> SEQ ID NO 264
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
uaguuccccc gagcaugga                                                19

<210> SEQ ID NO 265
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
aucacuuccg accugcugg                                                19

<210> SEQ ID NO 266
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
ccagcagguc ggaagugau                                                19

<210> SEQ ID NO 267
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
ggacaugugg agagccuac                                                19

<210> SEQ ID NO 268
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
guaggcucuc cacaugucc                                                19

<210> SEQ ID NO 269
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
```
cauguggaga gccuacucu                                             19

<210> SEQ ID NO 270
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
agaguaggcu cuccacaug                                             19

<210> SEQ ID NO 271
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
ggagagccua cucugacau                                             19

<210> SEQ ID NO 272
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
augucagagu aggcucucc                                             19

<210> SEQ ID NO 273
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
gagagccuac ucugacaug                                             19

<210> SEQ ID NO 274
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
caugucagag uaggcucuc                                             19

<210> SEQ ID NO 275
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275

```
uacucugaca ugagagaag                                                  19

<210> SEQ ID NO 276
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
cuucucucau gucagagua                                                  19

<210> SEQ ID NO 277
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
gaagccaauu acaucggcu                                                  19

<210> SEQ ID NO 278
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
agccgaugua auuggcuuc                                                  19

<210> SEQ ID NO 279
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gcucagacaa auacuucca                                                  19

<210> SEQ ID NO 280
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
uggaaguauu ugucugagc                                                  19

<210> SEQ ID NO 281
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
uacuuccaug cucggggga                                                  19
```

<210> SEQ ID NO 282
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282 uccccccgagc auggaagua                                               19

<210> SEQ ID NO 283
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
caccaugaag cuucucacg                                                19

<210> SEQ ID NO 284
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
cgugagaagc uucauggug                                                19

<210> SEQ ID NO 285
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
gccaaaaggg gaccugggg                                                19

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ccccaggucc ccuuuuggc                                                19

<210> SEQ ID NO 287
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
augaagcuuc ucacgggcc                                                19

<210> SEQ ID NO 288
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 288
ggcccgugag aagcuucau                                           19

<210> SEQ ID NO 289
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 289
gccauggugc ggaggacuc                                           19

<210> SEQ ID NO 290
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 290
gaguccuccg caccauggc                                           19

<210> SEQ ID NO 291
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 291
ccauggugcg gaggacucg                                           19

<210> SEQ ID NO 292
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 292
cgaguccucc gcaccaugg                                           19

<210> SEQ ID NO 293
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 293
cgggccuggu uuucugcuc                                           19

<210> SEQ ID NO 294
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 294
gagcagaaaa ccaggcccg                                               19

<210> SEQ ID NO 295
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 295
ugucagcagc cgaagcuuc                                               19

<210> SEQ ID NO 296
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 296
gaagcuucgg cugcugaca                                               19

<210> SEQ ID NO 297
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 297
gcagccgaag cuucuuuuc                                               19

<210> SEQ ID NO 298
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 298
gaaaagaagc uucggcugc                                               19

<210> SEQ ID NO 299
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 299
gcuucuuuuc guuccuugg                                               19

<210> SEQ ID NO 300

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
ccaaggaacg aaaagaagc                                                    19

<210> SEQ ID NO 301
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
uuccuuggcg aggcuuuug                                                    19

<210> SEQ ID NO 302
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
caaaagccuc gccaaggaa                                                    19

<210> SEQ ID NO 303
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
uccuuggcga ggcuuuuga                                                    19

<210> SEQ ID NO 304
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ucaaaagccu cgccaagga                                                    19

<210> SEQ ID NO 305
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
gaaauacuga gcuuccucu                                                    19

<210> SEQ ID NO 306
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
agaggaagcu caguauuuc                                                  19

<210> SEQ ID NO 307
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
accccaauca cuuccgacc                                                  19

<210> SEQ ID NO 308
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
ggucggaagu gauuggggu                                                  19

<210> SEQ ID NO 309
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
gggggaacua ugaugcugc                                                  19

<210> SEQ ID NO 310
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
gcagcaucau aguuccccc                                                  19

<210> SEQ ID NO 311
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
agacaaauac uuccaugcu                                                  19

<210> SEQ ID NO 312
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 312
agcauggaag uauuugucu                                                      19

<210> SEQ ID NO 313
<211> LENGTH: 21
<212> TYPE: RNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, u, t, g, unknown or other

<400> SEQUENCE: 313
agacaaauac uuccaugcun n                                                   21

<210> SEQ ID NO 314
<211> LENGTH: 21
<212> TYPE: RNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, u, t, g, unknown or other

<400> SEQUENCE: 314
agcauggaag uauuugucun n                                                   21

<210> SEQ ID NO 315
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
agacaaauac uuccaugcu                                                      19

<210> SEQ ID NO 316
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
agcauggaag uauuugucu                                                      19

<210> SEQ ID NO 317
<211> LENGTH: 21
<212> TYPE: DNA
```

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 317
agacaaauac uuccaugcut t                                             21

<210> SEQ ID NO 318
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 318
agcauggaag uauuugucut t                                             21
```

LIPID FORMULATED COMPOSITIONS AND METHODS FOR INHIBITING EXPRESSION OF SERUM AMYLOID A GENE

CROSS-REFERENCE TO RELATED APPLICATIONS

This application is a continuation of U.S. application Ser. No. 14/847,631, filed Dec. 19, 2017, now U.S. Pat. No. 10,472,628, issued Nov. 12, 2019, which is a continuation of U.S. application Ser. No. 14/932,782, filed Nov. 4, 2015, now U.S. Pat. No. 9,868,950, issued Jan. 16, 2018, which is a continuation of U.S. application Ser. No. 14/012,909, filed Aug. 28, 2013, now U.S. Pat. No. 9,206,421, issued Dec. 8, 2015, which is a continuation of U.S. application Ser. No. 13/120,601, filed Jun. 8, 2011, now U.S. Pat. No. 8,546,554, issued Oct. 1, 2013, which is a National Stage of International Application No. PCT/US2009/058480, filed Sep. 25, 2009, which claims the benefit of U.S. Provisional Application No. 61/100,195, filed Sep. 25, 2008; each application is herein incorporated in its entirety by reference.

SEQUENCE LISTING

The instant application contains a Sequence Listing with 318 sequences which has been submitted via EFS-Web and is hereby incorporated by reference in its entirety. Said ASCII copy, created on Sep. 23, 2019, is named AYL077C4_Sequence_Listing.txt, and is 88,269 bytes in size.

FIELD OF THE INVENTION

The invention relates to lipid formulated double-stranded ribonucleic acid (dsRNA) targeting a Serum Amyloid A (SAA) gene, and methods of using the dsRNA to inhibit expression of SAA.

BACKGROUND OF THE INVENTION

Serum Amyloid A (SAA) is an 104 amino acid HDL-associated apolipoprotein whose level in the blood is elevated up to 1000-fold in response to various injuries including trauma, inflammation and neoplasia. SAA proteins are involved in cholesterol metabolism and transport, inhibition of lymphocyte and endothelial cell proliferation, induction of matrix metalloproteinases, and modulation of the inflammatory response via both anti- and pro-inflammatory activities. Pro-inflammatory cytokines, such as IL-1β, IL-6, and TNFα, trigger inflammation and stimulate the production of acute-phase proteins, including SAA1 and SAA2.

Liver is the major site of SAA expression, and extrahepatic SAA expression has also been described in human atherosclerotic lesions, in the brains of Alzheimer disease patients, and in synovial tissues from rheumatoid arthritis patients. SAA levels have also been found to be elevated in the serum of patients with a wide range of malignancies, being highest in those with metastatic carcinoma of unknown primary sites. SAA mRNA and protein has also been found to be locally expressed in human colon carcinoma tissues and in epithelial carcinomas.

Four SAA loci, all mapped to chromosome 11p, have been described. Two of the loci (SAA1 and SAA2) encode acute-phase SAAs (A-SAAs), which exhibit a dramatic transient increase in serum concentration in response to inflammatory stimuli; a third locus (SAA3) defines a pseudogene; and a fourth locus (SAA4) encodes a constitutively expressed SAA (C-SAA), which responds only moderately to inflammatory stimuli. SAA3 is expressed in mice and other mammalian species, but is not expressed in humans. SAA1 and SAA2 are 95% homologous in both their coding and noncoding regions, and are coordinately induced in response to inflammation. The A-SAAs are the circulating precursors of the insoluble cleavage product amyloid A that is deposited in major organs in secondary amyloidosis (also called AA amyloidosis, or reactive amyloidosis), a progressive and fatal disease that is an occasional consequence of chronic or episodic inflammatory conditions such as rheumatoid arthritis and leprosy.

Double-stranded RNA molecules (dsRNA) have been shown to block gene expression in a highly conserved regulatory mechanism known as RNA interference (RNAi). WO 99/32619 (Fire et al.) disclosed the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., Curr. Biol. (2000) 10:1191-1200), and mammals (see WO 00/44895, Limmer; and DE 101 00 586.5, Kreutzer et al.).

SUMMARY OF THE INVENTION

The invention provides compositions containing double-stranded ribonucleic acid (dsRNA) and methods for inhibiting the expression of an SAA gene, such as one or both of SAA1 and SAA2, such as in a cell or mammal. The invention also provides compositions and methods for treating pathological conditions and diseases caused by the expression of an SAA gene, such as amyloidosis. The dsRNAs included in the compositions featured herein include a dsRNA having an RNA strand (the antisense strand) having a region that is less than 30 nucleotides in length, generally 19-24 nucleotides in length, and that is complementary to at least part of an mRNA transcript of an SAA gene.

In one embodiment, a dsRNA for inhibiting expression of an SAA gene includes at least two strands that are complementary to each other. The dsRNA includes a sense strand and an antisense strand. The antisense strand includes a nucleotide sequence that is complementary to at least part of an mRNA encoding SAA, and the region of complementarity is less than 30 nucleotides in length, and at least 15 nucleotides in length. Generally, the dsRNA is 19 to 24, e.g., 19 to 21 nucleotides in length. The dsRNA, upon contacting with a cell expressing SAA, inhibits the expression of an SAA gene by at least 40%, such as when assayed by a method as described herein.

For example, the dsRNA molecules featured herein can include a sense strand that is selected from the group consisting of the sense sequences of Table 2 and an antisense strand that is selected from the group consisting of the antisense sequences of Table 2. The dsRNA molecules featured herein can include naturally occurring nucleotides or can include at least one modified nucleotide, such as a 2'-O-methyl modified nucleotide, a nucleotide having a 5'-phosphorothioate group, and a terminal nucleotide linked to a cholesteryl derivative. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, such a modified sequence will be based on a first sequence of said dsRNA selected from the group consisting of the sense sequences of Table 2 and a second sequence selected from the group consisting of the antisense sequences of Table 2.

In an embodiment, the dsRNA can include a sense strand including at least 15 contiguous nucleotides of a sense strand sequence selected from Table 2. In an embodiment, the dsRNA can include an antisense strand including at least 15 contiguous nucleotides of an antisense sequence selected from Table 2.

In one embodiment, the sense strand can include 15 or more contiguous nucleotides of the nucleotide sequence of SEQ ID NO:37, SEQ ID NO:127, SEQ ID NO:95, SEQ ID NO:105, SEQ ID NO:59, SEQ ID NO:23, SEQ ID NO:155, SEQ ID NO:193, SEQ ID NO:283, SEQ ID NO:251, SEQ ID NO:261, SEQ ID NO:215, SEQ ID NO:179, or SEQ ID NO:311. In an embodiment, the antisense strand can include 15 or more contiguous nucleotides of the nucleotide sequence of SEQ ID NO:38, SEQ ID NO:128, SEQ ID NO:96, SEQ ID NO:106, SEQ ID NO:60, SEQ ID NO:24, SEQ ID NO:156, SEQ ID NO:194, SEQ ID NO:284, SEQ ID NO:252, SEQ ID NO:262, SEQ ID NO:216, SEQ ID NO:180, or SEQ ID NO:312. In another embodiment, the sense strand can consist of SEQ ID NO:37, SEQ ID NO:127, SEQ ID NO:95, SEQ ID NO:105, SEQ ID NO:59, SEQ ID NO:23, SEQ ID NO:155, SEQ ID NO:193, SEQ ID NO:283, SEQ ID NO:251, SEQ ID NO:261, SEQ ID NO:215, SEQ ID NO:179, or SEQ ID NO:311 and the antisense strand can consist of SEQ ID NO:38, SEQ ID NO:128, SEQ ID NO:96, SEQ ID NO:106, SEQ ID NO:60, SEQ ID NO:24, SEQ ID NO:156, SEQ ID NO:194, SEQ ID NO:284, SEQ ID NO:252, SEQ ID NO:262, SEQ ID NO:216, SEQ ID NO:180, or SEQ ID NO:312. In an embodiment, the dsRNA is 18397, 18379, 18445, 18420, 18415, 18431, or 18326. In an embodiment, the dsRNA targets SEQ ID NO:193, SEQ ID NO:283, SEQ ID NO:251, SEQ ID NO:261, SEQ ID NO:215, SEQ ID NO:179, or SEQ ID NO:311.

In an embodiment, the dsRNA is conjugated to a ligand. In an embodiment, the dsRNA is formulated in a lipid formulation. In an embodiment, the dsRNA is formulated in a LNP formulation, a LNP01 formulation, a LIPID A-SNALP formulation, or a SNALP formulation.

In an embodiment, administration of the dsRNA to a cell results in about 97%, 95%, 92%, 89%, or 74% inhibition of SAA mRNA expression as measured by a real time PCR assay. In an embodiment, administration of the dsRNA to a cell results in about 89%, 87%, 83%, 68%, or 54% inhibition of SAA mRNA expression as measured by a branched DNA assay. In an embodiment, administration of the dsRNA to a cell results in about 100%, 99%, or 93% inhibition of SAA protein expression as measured by an ELISA assay. In an embodiment, the dsRNA has an IC50 of less than 10 pM. In an embodiment, administration of the dsRNA reduces SAA protein expression by about 80% in mice compared to an siRNA control.

In an embodiment, the dsRNA includes an overhang. In an embodiment, the dsRNA includes a dTdT overhang. In an embodiment, the dsRNA comprises two dTdT overhangs on the 3' end of the sense strand and the antisense strand.

In an embodiment, the sense strand is 21 nucleotides in length. In an embodiment, the antisense strand is 21 nucleotides in length. In an embodiment, the dsRNA comprises one or more 2'-O-methylcytidine-5'-phosphates and/or one or more 2'-O-methyluridine-5'-phosphates.

In another embodiment, the invention provides a cell containing at least one of the dsRNAs featured in the invention. The cell is generally a mammalian cell, such as a human cell.

In another embodiment, the invention provides a pharmaceutical composition for inhibiting the expression of an SAA gene in an organism, generally a human subject. The composition typically includes one or more of the dsRNAs described herein and a pharmaceutically acceptable carrier or delivery vehicle. In one embodiment, the composition is used for treating amyloidosis, e.g., AA (secondary or reactive) amyloidosis.

In another embodiment, the pharmaceutical composition is formulated for administration of a dosage regimen described herein, e.g., not more than once every four weeks, not more than once every three weeks, not more than once every two weeks, or not more than once every week. In another embodiment, the pharmaceutical composition can be maintained for a month or longer, e.g., one, two, three, or six months, or one year or longer.

In another embodiment, a composition containing a dsRNA featured in the invention, i.e., a dsRNA targeting SAA, is administered with a non-dsRNA therapeutic agent, such as an agent known to treat amyloidosis, or a symptom of amyloidosis. For example, a dsRNA featured in the invention can be administered with an agent for treatment of an inflammatory disorder, such as chronic inflammatory arthritis, or an agent for treatment of renal dysfunction. Exemplary agents for treatment of chronic inflammatory arthritis include anti-cytokine biologics, such as anakinra, tocilizumab, etanercept, infliximab, adlimumab, certolizumab, rituxan, rituximab, chlorambucil, and Eprodisate (Neurochem, Canada). Exemplary agents for treatment of renal dysfunction include, e.g., diuretics, ACE (Angiotensin-Converting Enzyme) inhibitors, ARBs (angiotensin receptor blocking agents), dialysis in end stage renal disease (ESRD), and renal transplant.

In another embodiment, an SAA dsRNA is administered to a patient, and then the non-dsRNA agent is administered to the patient (or vice versa). In another embodiment, an SAA dsRNA and the non-dsRNA therapeutic agent are administered at the same time.

In another embodiment, the invention provides a method for inhibiting the expression of an SAA gene in a cell by performing the following steps:

(a) introducing into the cell a double-stranded ribonucleic acid (dsRNA), wherein the dsRNA includes at least two sequences that are complementary to each other. The dsRNA has a sense strand having a first sequence and an antisense strand having a second sequence; the antisense strand has a region of complementarity that is complementary to at least a part of an mRNA encoding SAA, and where the region of complementarity is less than 30 nucleotides in length, generally 19-24 nucleotides in length, and where the dsRNA, upon contact with a cell expressing an SAA, inhibits expression of an SAA gene by at least 40%;

and (b) maintaining the cell produced in step (a) for a time sufficient to obtain degradation of the mRNA transcript of SAA gene, thereby inhibiting expression of an SAA gene in the cell.

In another embodiment, the method is for inhibiting gene expression in a tumor cell.

In another embodiment, the invention provides methods for treating, preventing or managing pathological processes mediated by SAA expression, such as amyloidosis, e.g., AA amyloidosis. In one embodiment, the method includes administering to a patient in need of such treatment, prevention or management a therapeutically or prophylactically effective amount of one or more of the dsRNAs featured in the invention. In one embodiment the patient has amyloidosis. In another embodiment, administration of the dsRNA targeting SAA alleviates or relieves the severity of at least one symptom of an SAA-mediated disorder in the patient. In one embodiment the patient has psoriatic arthritis, chronic juvenile arthritis, ankylosing spondylitis, Behcet's syndrome, Reiter's syndrome, adult Still's disease, inflammatory bowel disease, hereditary periodic fevers, tuberculosis, osteomyelitis, bronchiectasis, leprosy, pyelonephritis, decubitus ulcers, Whipple's disease, acne conglobata, common variable immunodeficiency hypo/agammaglobulinemia, cystic fibrosis, hepatoma, renal carcinoma, Castleman's disease, Hodgkin's disease, adult hairy cell leukemia, Waldenstrom's disease, a neoplasm, a chronic infections, a chronic inflammatory disease, chronic arthritis, chronic sepsis, a periodic fever syndrome, familial Mediterranean fever, or Crohn's disease.

In another embodiment, the invention provides a vector for inhibiting the expression of an SAA gene in a cell. In one embodiment, the vector includes at least one regulatory sequence operably linked to a nucleotide sequence that encodes at least one strand of a dsRNA featured in the invention.

In another embodiment, the invention provides a cell containing a vector for inhibiting the expression of an SAA gene in a cell. The vector includes a regulatory sequence operably linked to a nucleotide sequence that encodes at least one strand of one of the dsRNA featured in the invention.

In a further embodiment, the invention provides a composition containing an SAA dsRNA, in combination with a second dsRNA targeting a second gene involved in a pathological disease, and useful for treating the disease, e.g., amyloidosis.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 4A is a graph illustrating dose response curves for selected SAA siRNAs.

FIG. 4B is a graph illustrating dose response curves for selected SAA siRNAs.

FIG. 4C is a graph illustrating dose response curves for selected SAA siRNAs.

FIG. 4D is a graph illustrating dose response curves for selected SAA siRNAs.

FIG. 4E is a graph illustrating dose response curves for selected SAA siRNAs.

FIG. 4F is a graph illustrating dose response curves for selected SAA siRNAs.

FIG. 4G is a graph illustrating dose response curves for selected SAA siRNAs.

FIG. 5 is a graph showing that SAA levels were increased in all mice tested 24 hours after LPS injection compared to pre-LPS injection SAA levels.

DETAILED DESCRIPTION OF THE INVENTION

Figure 1A:
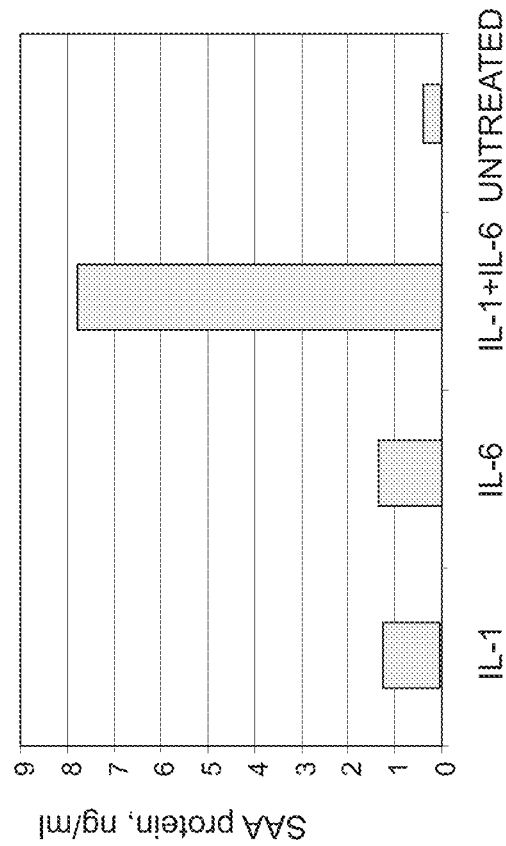
FIG. 1A is a graph showing the effect of IL-1β and IL-6 cytokines on SAA mRNA and protein levels in HepB3 cell culture.

The invention provides dsRNAs and methods of using the dsRNAs for inhibiting the expression of an SAA gene in a cell or a mammal where the dsRNA targets an SAA gene. In some embodiments, the dsRNAs featured in the invention target both an SAA1 gene and an SAA2 gene. The invention also provides compositions and methods for treating pathological conditions and diseases, such as an amyloidosis, in a mammal caused by the expression of an SAA gene. dsRNA directs the sequence-specific degradation of mRNA through a process known as RNA interference (RNAi).

The dsRNAs of the compositions featured herein include an RNA strand (the antisense strand) having a region which is less than 30 nucleotides in length, generally 19-24 nucleotides in length, and is substantially complementary to at least part of an mRNA transcript of an SAA gene. The use of these dsRNAs enables the targeted degradation of mRNAs of genes that are implicated in pathologies associated with an inflammatory response (e.g., an acute phase inflammatory response) in mammals. Very low dosages of SAA dsRNAs in particular can specifically and efficiently mediate RNAi, resulting in significant inhibition of expression of an SAA gene. Using cell-based assays, the present inventors have demonstrated that dsRNAs targeting SAA can specifically and efficiently mediate RNAi, resulting in significant inhibition of expression of an SAA gene. Thus, methods and compositions including these dsRNAs are useful for treating pathological processes that can be mediated by down regulating SAA, such as in the treatment of amyloidosis.

The dsRNAs of the compositions can include a sense strand including at least 15, 16, 17, 18, 19, 20, or 21 or more nucleotides of a sense strand sequence selected from Table 2. The dsRNAs of the compositions can include an antisense strand including at least 15, 16, 17, 18, 19, 20, or 21 or more nucleotides of a sense strand sequence selected from Table 2. In an embodiment, the sense strand can include 15, 16, 17, 18, 19, 20, or 21 or more contiguous nucleotides of SEQ ID NO:37, SEQ ID NO:127, SEQ ID NO:95, SEQ ID NO:105, SEQ ID NO:59, SEQ ID NO:23, or SEQ ID NO:155. In an embodiment, the antisense strand can include 15, 16, 17, 18, 19, 20, or 21 or more contiguous nucleotides of SEQ ID NO:38, SEQ ID NO:128, SEQ ID NO:96, SEQ ID NO:106, SEQ ID NO:60, SEQ ID NO:24, or SEQ ID NO:156.

The dsRNAs of the compositions can target 15, 16, 17, 18, 19, 20, or 21 or more contiguous nucleotides of a SAA mRNA, SEQ ID NO:286, SEQ ID NO:220, SEQ ID NO:230, SEQ ID NO:324, SEQ ID NO:223, SEQ ID NO:386, and/or SEQ ID NO:373.

The dsRNA can be conjugated to a ligand. The dsRNA can be formulated in a lipid formulation. In an embodiment, the dsRNA is formulated in a LNP formulation, a LNP01 formulation, a Lipid A-SNALP formulation, or a SNALP formulation.

The dsRNAs of the compositions, when administered to a cell, can result in about 50-100%, 97%, 95%, 92%, 89%, or 74% inhibition of SAA mRNA expression as measured by a real time PCR assay. The dsRNAs of the compositions, when administered to a cell, can result in about 50-100%, 89%, 87%, 83%, 68%, or 54% inhibition of SAA mRNA expression as measured by a branched DNA assay. The dsRNAs of the compositions, when administered to a cell, can result in about 50-100%, 100%, 99%, or 93% inhibition of SAA protein expression as measured by an ELISA assay. The dsRNAs of the compositions have an IC50 of less than 1, 2, 3, 4, 5, 6, 7, 8, 9, 10, 11, 12, 13, 14, or 15 pM. The dsRNAs of the compositions can reduce SAA protein expression by about 40, 50, 60, 70, 80, or 90% in mice compared to an siRNA control.

The methods and compositions containing an SAA dsRNA are useful for treating pathological processes mediated by SAA expression, such as inflammation-associated disorders, such as amyloidosis. Other pathological processes can include psoriatic arthritis, chronic juvenile arthritis, ankylosing spondylitis, Behcet's syndrome, Reiter's syndrome, adult Still's disease, inflammatory bowel disease, hereditary periodic fevers, tuberculosis, osteomyelitis, bronchiectasis, leprosy, pyelonephritis, decubitus ulcers, Whipple's disease, acne conglobata, common variable immunodeficiency hypo/agammaglobulinemia, cystic fibrosis, hepatoma, renal carcinoma, Castleman's disease, Hodgkin's disease, adult hairy cell leukemia, Waldenstrom's disease, a neoplasm, a chronic infections, a chronic inflammatory disease, chronic arthritis, chronic sepsis, a periodic fever syndrome, familial Mediterranean fever, or Crohn's disease.

The following detailed description discloses how to make and use the compositions containing dsRNAs to inhibit the expression of an SAA gene, as well as compositions and methods for treating diseases and disorders caused by the expression of these genes. The pharmaceutical compositions featured in the invention include a dsRNA having an antisense strand comprising a region of complementarity which is less than 30 nucleotides in length, generally 19-24 nucleotides in length, and is substantially complementary to at least part of an RNA transcript of an SAA gene, together with a pharmaceutically acceptable carrier. The compositions featured in the invention also include a dsRNA having an antisense strand having a region of complementarity which is less than 30 nucleotides in length, generally 19-24 nucleotides in length, and is substantially complementary to at least part of an RNA transcript of an SAA gene.

Accordingly, in some aspects, pharmaceutical compositions containing an SAA dsRNA and a pharmaceutically acceptable carrier, methods of using the compositions to inhibit expression of an SAA gene, and methods of using the pharmaceutical compositions to treat diseases caused by expression of an SAA gene are featured in the invention.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, "Serum Amyloid A" ("SAA") refers to an SAA1 or an SAA2 gene (e.g., an endogenous SAA1 or SAA2 gene) in a cell. SAA1 is also known as serum amyloid A1, MGC111216, PIG4, SAA, and tumor protein p53 inducible protein 4 (TP53I4). The sequence of two alternative human SAA1 mRNA transcripts can be found at NM_000331.3 and NM_199161.2. The sequence of mouse SAA1 mRNA can be found at NM_009117.3. A single, near full length, SAA-like trace cDNA sequence from cynomolgus monkey is Mfa #527795076 (*Macaca fascicularis*).

SAA2 is also known as serum amyloid A2 and SAA. The sequence of two alternative human SAA2 mRNA transcripts can be found at NM_001127380.1 and NM_030754.3. The sequence of mouse SAA2 mRNA is at NM_011314.1.

As used herein, "target sequence" refers to a contiguous portion of the nucleotide sequence of an mRNA molecule formed during the transcription of an SAA gene, including mRNA that is a product of RNA processing of a primary transcription product. The target sequence is complementary to the dsRNA antisense sequence and thus has the same sequence as the dsRNA sense sequence, minus any overhang that is present in the sense strand.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide that is "substantially complementary to at least part of a messenger RNA (mRNA) refers to a polynucleotide that is substantially complementary to a contiguous portion of the mRNA of interest (e.g., an mRNA encoding SAA, such as SAA1 or SAA2) including a 5" UTR, an open reading frame (ORF), or a 3' UTR. For example, a polynucleotide is complementary to at least a part of an SAA mRNA if the sequence is substantially complementary to a non-interrupted portion of an mRNA encoding SAA.

The term "double-stranded RNA" or "dsRNA," as used herein, refers to a complex of ribonucleic acid molecules, having a duplex structure comprising two anti-parallel and substantially complementary, as defined above, nucleic acid strands. In general, the majority of nucleotides of each strand are ribonucleotides, but as described in detail herein, each or both strands can also include at least one non-ribonucleotide, e.g., a deoxyribonucleotide and/or a modified nucleotide. In addition, as used in this specification, "dsRNA" may include chemical modifications to ribonucleotides, including substantial modifications at multiple nucleotides and including all types of modifications disclosed herein or known in the art. Any such modifications, as used in an siRNA type molecule, are encompassed by "dsRNA" for the purposes of this specification and claims.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'end of the respective other strand forming the duplex structure, the connecting RNA chain is referred to as a "hairpin loop." Where the two strands are connected covalently by means other than an uninterrupted chain of nucleotides between the 3'-end of one strand and the 5' end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. The term "siRNA" is also used herein to refer to a dsRNA as described above.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule. In an embodiment, the sequences shown in the "Sequence without chemistry (5'-3')" column of Table 2 (SAA siRNAs; below) can include one or more overhangs comprised of one or more nucleotides. In one aspect, the overhang is a two nucleotide 3' overhang comprising the sequence NN, where NN can be any nucleotide, e.g., C, A, G, T. In an embodiment, the overhang can include one or more phosphorothioates on the overhang, e.g., the terminal 3' dT of the overhang can have a phosphorothioate. In an embodiment, the overhang is dTsdT.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

"Introducing into a cell," when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell," wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence," "inhibit the expression of," "down-regulate the expression of," "suppress the expression of" and the like in as far as they refer to an SAA gene, herein refer to the at least partial suppression of the expression of an SAA gene, as manifested by a reduction of the amount of mRNA which may be isolated and/or detected from a first cell or group of cells in which an SAA gene is transcribed and which has or have been treated such that the expression of an SAA gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to SAA gene transcription, e.g., the amount of protein encoded by an SAA gene which is secreted by a cell, or the number of cells displaying a certain phenotype, e.g., apoptosis. In principle, SAA gene silencing may be determined in any cell expressing the target, either constitutively or by genomic engineering, and by any appropriate assay. However, when a reference is needed in order to determine whether a given dsRNA inhibits the expression of an SAA gene by a certain degree and therefore is encompassed by the instant invention, the assays provided in the Examples below shall serve as such reference.

For example, in certain instances, expression of an SAA gene is suppressed by at least about 5%, 10%, 15%, 20%, 25%, 30%, 35%, 40%, 45%, or 50% by administration of the double-stranded oligonucleotide featured in the invention. In some embodiments, an SAA gene is suppressed by at least about 60%, 70%, or 80% by administration of the double-stranded oligonucleotide featured in the invention. In some embodiments, an SAA gene is suppressed by at least about 85%, 90%, or 95% by administration of the double-stranded oligonucleotide featured in the invention. Tables 3, 4, and 5, and FIGS. 2 and 3 indicate a range of inhibition of expression obtained in in vitro and ex vivo assays using various SAA dsRNA molecules at various concentrations.

As used herein in the context of SAA expression, the terms "treat," "treatment," and the like, refer to relief from or alleviation of pathological processes mediated by SAA expression. In the context of the present invention insofar as it relates to any of the other conditions recited herein below (other than pathological processes mediated by SAA expression), the terms "treat," "treatment," and the like mean to relieve or alleviate at least one symptom associated with such condition, or to slow or reverse the progression of such condition, such as the slowing and progression of amyloidosis.

As used herein, the phrases "therapeutically effective amount" and "prophylactically effective amount" refer to an amount that provides a therapeutic benefit in the treatment, prevention, or management of pathological processes mediated by SAA expression or an overt symptom of pathological processes mediated by SAA expression. The specific amount that is therapeutically effective can be readily determined by an ordinary medical practitioner, and may vary depending on factors known in the art, such as, for example, the type of pathological processes mediated by SAA expression, the patient's history and age, the stage of pathological processes mediated by SAA expression, and the administration of other anti-pathological processes mediated by SAA expression agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of a RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter. For example, a therapeutically effective amount of a dsRNA targeting SAA can reduce SAA serum levels by at least 25%. In another example, a therapeutically effective amount of a dsRNA targeting SAA can improve renal function by at least 25%.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. Double-Stranded Ribonucleic Acid (dsRNA)

As described in more detail herein, the invention provides double-stranded ribonucleic acid (dsRNA) molecules for inhibiting the expression of an SAA gene in a cell or mammal, e.g., in a human having an amyloidosis, where the dsRNA includes an antisense strand having a region of complementarity which is complementary to at least a part of an mRNA formed in the expression of an SAA gene, and where the region of complementarity is less than 30 nucleotides in length, generally 19-24 nucleotides in length, and where said dsRNA, upon contact with a cell expressing said SAA gene, inhibits the expression of said SAA gene by at least 30% as assayed by, for example, a PCR or branched DNA (bDNA)-based method, or by a protein-based method, such as by Western blot. Expression of an SAA gene can be reduced by at least 30% when measured by an assay as described in the Examples below. For example, expression of an SAA gene in cell culture, such as in HepB3 cells, can be assayed by measuring SAA mRNA levels, such as by bDNA or TaqMan assay, or by measuring protein levels, such as by ELISA assay. The dsRNA of the invention can further include one or more single-stranded nucleotide overhangs.

The dsRNA can be synthesized by standard methods known in the art as further discussed below, e.g., by use of an automated DNA synthesizer, such as are commercially available from, for example, Biosearch, Applied Biosystems, Inc. The dsRNA includes two RNA strands that are sufficiently complementary to hybridize to form a duplex structure. One strand of the dsRNA (the antisense strand) includes a region of complementarity that is substantially complementary, and generally fully complementary, to a target sequence, derived from the sequence of an mRNA formed during the expression of an SAA gene, the other strand (the sense strand) includes a region that is complementary to the antisense strand, such that the two strands hybridize and form a duplex structure when combined under suitable conditions. Optionally, the region of the antisense strand that is substantially complementary to a sequence of an SAA mRNA is substantially complementary to both an SAA1 and an SAA2 mRNA. Generally, the duplex structure is between 15 and 30, more generally between 18 and 25, yet more generally between 19 and 24, and most generally between 19 and 21 base pairs in length. Similarly, the region of complementarity to the target sequence is between 15 and 30, or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length. When two different siRNAs are used in combination, the duplex lengths can be identical or can differ.

Each strand of the dsRNA of invention is generally between 15 and 30, or between 18 and 25, or 18, 19, 20, 21, 22, 23, 24, or 25 nucleotides in length. In other embodiments, each is strand is 25-30 nucleotides in length. Each strand of the duplex can be the same length or of different lengths. When two different siRNAs are used in combination, the lengths of each strand of each siRNA can be identical or can differ.

The dsRNA of the invention can include one or more single-stranded overhang(s) of one or more nucleotides. In one embodiment, at least one end of the dsRNA has a single-stranded nucleotide overhang of 1 to 4, generally 1 or 2 nucleotides. In another embodiment, the antisense strand of the dsRNA has 1-10 nucleotides overhangs each at the 3' end and the 5' end over the sense strand. In further embodiments, the sense strand of the dsRNA has 1-10 nucleotides overhangs each at the 3' end and the 5' end over the antisense strand.

'Generally, the dsRNA includes two 3' overhangs. In an embodiment, the antisense strand of the dsRNA has a nucleotide overhang at the 3'-end, and the 5'-end is blunt. In another embodiment, the sense strand of the dsRNA has a nucleotide overhang at the 3' end and the 5' end is blunt. In another embodiment, both ends of the dsRNA can be blunt. In another embodiment, one or more of the nucleotides in the overhang is replaced with a nucleoside thiophosphate.

In one embodiment, an SAA gene is a human SAA gene. In specific embodiments, the sense strand of the dsRNA is one of the sense sequences from Table 2, and the antisense strand is one of the antisense sequences of Table 2. Alternative antisense agents that target elsewhere in the target sequence provided in Table 2 can readily be determined using the target sequence and the flanking SAA sequence.

The skilled person is well aware that dsRNAs having a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Table 2, the dsRNAs featured in the invention can include at least one strand of a length described therein. It can be reasonably expected that shorter dsRNAs having one of the sequences of Table 2 minus only a few nucleotides on one or both ends may be similarly effective as compared to the dsRNAs described above. Hence, dsRNAs having a partial sequence of at least 15, 16, 17, 18, 19, 20, 21, or 22 or more contiguous nucleotides from one of the sequences of Table 2, and differing in their ability to inhibit the expression of an SAA gene in an assay as described herein below by not more than 5, 10, 15, 20, 25, or 30% inhibition from a dsRNA comprising the full sequence, are contemplated by the invention. Further, dsRNAs that cleave within a desired SAA target sequence can readily be made using the corresponding SAA antisense sequence and a complementary sense sequence.

In addition, the dsRNAs provided in Table 2 identify a site in an SAA mRNA (e.g., in an SAA1 and/or an SAA2 mRNA) that is susceptible to RNAi based cleavage. As such, the present invention further features dsRNAs that target within the sequence targeted by one of the agents of the present invention. As used herein, a second dsRNA is said to target within the sequence of a first dsRNA if the second dsRNA cleaves the message anywhere within the mRNA that is complementary to the antisense strand of the first dsRNA. Such a second dsRNA will generally consist of at least 15 contiguous nucleotides from one of the sequences provided in Table 2 coupled to additional nucleotide sequences taken from the region contiguous to the selected sequence in an SAA1 or SAA2 gene. For example, the last 15 nucleotides of SEQ ID NO:1 combined with the next six nucleotides from the target SAA gene produces a single strand agent of 21 nucleotides that is based on one of the sequences provided in Table 2.

The dsRNA featured in the invention can contain one or more mismatches to the target sequence. In one embodiment, the dsRNA featured the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of an SAA gene, the dsRNA generally does not contain any mismatch within the central 13 nucleotides. The methods described within the invention can be used to determine whether a dsRNA containing a mismatch to a target sequence is effective in inhibiting the expression of an SAA gene. Consideration of the efficacy of dsRNAs with mismatches in inhibiting expression of an SAA gene is important, especially if the particular region of complementarity in an SAA gene is known to have polymorphic sequence variation within the population.

Modifications

In yet another embodiment, the dsRNA is chemically modified to enhance stability. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Specific examples of dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,195; 5,188,897; 5,264,423; 5,276, 019; 5,278,302; 5,286,717; 5,321,131; 5,399,676; 5,405, 939; 5,453,496; 5,455,233; 5,466,677; 5,476,925; 5,519, 126; 5,536,821; 5,541,316; 5,550,111; 5,563,253; 5,571, 799; 5,587,361; and 5,625,050, each of which is herein incorporated by reference Modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other suitable dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, a dsRNA mimetic that has been shown to have excellent hybridization properties, is referred to as a peptide nucleic acid (PNA). In PNA compounds, the sugar backbone of a dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Other embodiments of the invention are dsRNAs with phosphorothioate backbones and oligonucleosides with heteroatom backbones, and in particular —CH$_2$—NH—CH$_2$—, —CH$_2$—N(CH$_3$)—O—CH$_2$— [known as a methylene (methylimino) or MMI backbone], —CH$_2$—O—N (CH$_3$)—CH$_2$—, —CH$_2$—N(CH$_3$)—N(CH$_3$)—CH$_2$— and —N(CH$_3$)—CH$_2$—CH$_2$— [wherein the native phosphodiester backbone is represented as —O—P—O—CH$_2$—] of the above-referenced U.S. Pat. No. 5,489,677, and the amide backbones of the above-referenced U.S. Pat. No. 5,602,240. Also preferred are dsRNAs having morpholino backbone structures of the above-referenced U.S. Pat. No. 5,034,506.

Modified dsRNAs may also contain one or more substituted sugar moieties. Preferred dsRNAs comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred dsRNAs comprise one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. A preferred modification includes 2'-methoxyethoxy (2'-O—CH2CH2OCH3, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2—O—CH2—N(CH2)2, also described in examples herein below.

Other preferred modifications include 2'-methoxy (2'-OCH$_3$), 2'-aminopropoxy (2'-OCH$_2$CH$_2$CH$_2$NH$_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393, 878; 5,446,137; 5,466,786; 5,514,785; 5,519,134; 5,567, 811; 5,576,427; 5,591,722; 5,597,909; 5,610,300; 5,627, 053; 5,639,873; 5,646,265; 5,658,873; 5,670,633; and 5,700,920, certain of which are commonly owned with the instant application, and each of which is herein incorporated by reference in its entirety.

dsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., DsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, each of which is herein incorporated by reference, and U.S. Pat. No. 5,750,692, also herein incorporated by reference.

Conjugates

Another modification of the dsRNAs featured in the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylaminocarbonyloxycholesterol moiety (Crooke et al., J. Pharmacol. Exp. Ther., 1996, 277:923-937).

Representative U.S. patents that teach the preparation of such dsRNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within a dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of a dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, Rnase H is a cellular endonuclease which cleaves the RNA strand of an RNA:DNA duplex. Activation of Rnase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region.

Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

Vector Encoded dsRNAs

In another aspect, SAA dsRNA molecules are expressed from transcription units inserted into DNA or RNA vectors (see, e.g., Couture, A, et al., TIG. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., Proc. Natl. Acad. Sci. USA (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In one embodiment, a dsRNA is expressed as an inverted repeat joined by a linker polynucleotide sequence such that the dsRNA has a stem and loop structure.

The recombinant dsRNA expression vectors are generally DNA plasmids or viral vectors. dsRNA expressing viral vectors can be constructed based on, but not limited to, adeno-associated virus (for a review, see Muzyczka, et al., Curr. Topics Micro. Immunol. (1992) 158:97-129)); adenovirus (see, for example, Berkner, et al., BioTechniques (1998) 6:616), Rosenfeld et al. (1991, Science 252:431-434), and Rosenfeld et al. (1992), Cell 68:143-155)); or alphavirus as well as others known in the art. Retroviruses have been used to introduce a variety of genes into many different cell types, including epithelial cells, in vitro and/or in vivo (see, e.g., Eglitis, et al., Science (1985) 230:1395-1398; Danos and Mulligan, Proc. Natl. Acad. Sci. USA (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. Et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Any viral vector capable of accepting the coding sequences for the dsRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors featured in the invention can be pseudotyped with surface proteins from vesicular stomatitis virus (VSV), rabies, Ebola, Mokola, and the like. AAV vectors featured in the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Viral vectors can be derived from AV and AAV. In one embodiment, the dsRNA featured in the invention is expressed as two separate, complementary single-stranded RNA molecules from a recombinant AAV vector having, for example, either the U6 or H1 RNA promoters, or the cytomegalovirus (CMV) promoter.

A suitable AV vector for expressing the dsRNA featured in the invention, a method for constructing the recombinant AV vector, and a method for delivering the vector into target cells, are described in Xia H et al. (2002), Nat. Biotech. 20: 1006-1010.

Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

The promoter driving dsRNA expression in either a DNA plasmid or viral vector featured in the invention may be a eukaryotic RNA polymerase I (e.g., ribosomal RNA promoter), RNA polymerase II (e.g., CMV early promoter or actin promoter or U1 snRNA promoter) or generally RNA polymerase III promoter (e.g., U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g., the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g., Oligofectamine) or non-cationic lipid-based carriers (e.g., Transit-TKO™). Multiple lipid transfections for dsRNA-mediated knockdowns targeting different regions of a single SAA gene or multiple SAA genes over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

SAA specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

III. Pharmaceutical Compositions Containing dsRNA

In one embodiment, the invention provides pharmaceutical compositions containing a dsRNA, as described herein, and a pharmaceutically acceptable carrier. The pharmaceutical composition containing the dsRNA is useful for treating a disease or disorder associated with the expression or activity of an SAA gene, such as pathological processes mediated by SAA expression. Such pharmaceutical compositions are formulated based on the mode of delivery. One example is compositions that are formulated for systemic administration via parenteral delivery, e.g., by intravenous (IV) delivery. Another example is compositions that are formulated for direct delivery into the brain parenchyma, e.g., by infusion into the brain, such as by continuous pump infusion.

In general, a suitable dose of dsRNA will be in the range of 0.01 to 200.0 milligrams per kilogram body weight of the recipient per day, generally in the range of 0.1 to 50 or 0.1 to 5.0 mg per kilogram body weight per day. For example, the dsRNA can be administered at 0.01 mg/kg, 0.05 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 3 mg/kg, 5.0 mg/kg, 10 mg/kg, 20 mg/kg, 30 mg/kg, 40 mg/kg, or 50 mg/kg per single dose. The pharmaceutical composition may be administered once daily or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art and are particularly useful for delivery of agents at a particular site, such as could be used with the agents of the present invention. In this embodiment, the dosage unit contains a corresponding multiple of the daily dose.

The effect of a single dose on SAA levels (or both SAA1 and SAA2 levels) is long lasting, such that subsequent doses are administered at not more than 3, 4, or 5 day intervals, or at not more than 1, 2, 3, or 4 week intervals.

The present invention includes pharmaceutical compositions that can be delivered by injection directly into the brain. The injection can be by stereotactic injection into a particular region of the brain (e.g., the substantia nigra, cortex, hippocampus, striatum, or globus pallidus), or the dsRNA can be delivered into multiple regions of the central nervous system (e.g., into multiple regions of the brain, and/or into the spinal cord). The dsRNA can also be delivered into diffuse regions of the brain (e.g., diffuse delivery to the cortex of the brain).

In one embodiment, a dsRNA targeting SAA can be delivered by way of a cannula or other delivery device having one end implanted in a tissue, e.g., the brain, e.g., the substantia nigra, cortex, hippocampus, striatum, corpus callosum or globus pallidus of the brain. The cannula can be connected to a reservoir of the dsRNA composition. The flow or delivery can be mediated by a pump, e.g., an osmotic pump or minipump, such as an Alzet pump (Durect, Cupertino, Calif.). In one embodiment, a pump and reservoir are implanted in an area distant from the tissue, e.g., in the abdomen, and delivery is effected by a conduit leading from the pump or reservoir to the site of release. Infusion of the dsRNA composition into the brain can be over several hours or for several days, e.g., for 1, 2, 3, 5, or 7 days or more. Devices for delivery to the brain are described, for example, in U.S. Pat. Nos. 6,093,180, and 5,814,014.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by SAA expression. Such models are used for in vivo testing of dsRNA, as well as for determining a therapeutically effective dose. A suitable mouse model is, for example, a mouse containing a plasmid expressing human SAA1 or SAA2, e.g., from an adenoviral vector. Another suitable mouse model is a transgenic mouse carrying a transgene that expresses human SAA1 or SAA2.

The data obtained from cell culture assays and animal studies can be used in formulating a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The dsRNAs featured in the invention can be administered in combination with other known agents effective in treatment of pathological processes mediated by target gene expression. In any event, the administering physician can adjust the amount and timing of dsRNA administration on the basis of results observed using standard measures of efficacy known in the art or described herein.

Administration

The present invention also includes pharmaceutical compositions and formulations which include the dsRNA compounds featured in the invention. The pharmaceutical compositions of the present invention may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intraparenchymal, intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the dsRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). DsRNAs featured in the invention may be encapsulated within liposomes or may form complexes thereto, in particular to cationic liposomes. Alternatively, dsRNAs may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a C1-10 alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers, surfactants, and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference in their entirety.

Compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

Liposomal Formulations

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/po-lyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P.Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside GM1, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside GM1 or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, 2C1215G, that contains a PEG moiety. Ilium et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

SNALPs

In one embodiment, a dsRNA featured in the invention is fully encapsulated in the lipid formulation to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1, or 5:1, 6:1, 7:1, 8:1, 9:1, 10:1, or 11:1.

The cationic lipid may be, for example, N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethyl-ammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (Dlin-C-DAP), 1,2-Dilinoleyoxy-3-(dimethylamino)acetoxypropane (Dlin-DAC), 1,2-Dilinoleyoxy-3-morpholinopropane (Dlin-MA), 1,2-Dilinoleoyl-3-dimethylaminopropane (DLin-DAP), 1,2-Dilinoleylthio-3-dimethylaminopropane (Dlin-S-DMA), 1-Linoleoyl-2-linoleyloxy-3-dimethylaminopropane (Dlin-2-DMAP), 1,2-Dilinoleyloxy-3-trimethylaminopropane chloride salt (Dlin-TMA.Cl), 1,2-Dilinoleoyl-3-trimethylaminopropane chloride salt (Dlin-TAP.Cl), 1,2-Dilinoleyloxy-3-(N-methylpiperazino)propane (Dlin-MPZ), or 3-(N,N-Dilinoleylamino)-1,2-propanediol (DlinAP), 3-(N,N-Dioleylamino)-1,2-propanedio (DOAP), 1,2-Dilinoleyloxo-3-(2-N,N-dimethylamino)ethoxypropane (Dlin-EG-DMA), 1,2-Dilinolenyloxy-N,N-dimethylaminopropane (DLinDMA), 2,2-Dilinoleyl-4-dimethylaminomethyl-[1,3]-dioxolane (Dlin-K-DMA) or analogs thereof, or a mixture thereof. The cationic lipid may comprise from about 20 mol % to about 60 mol % or about 40 mol %, 50 mol %, 51 mol %, 52 mol %, 53 mol %, 54 mol %, 55 mol %, 56 mol %, 57 mol %, 58 mol %, 59 mol %, or 60 mol %,of the total lipid present in the particle.

In another embodiment, the cationic lipid 2,2-Dilinoleyl-4-dimethylaminoethyl-[1,3]-dioxolane (Lipid A) can be used to prepare lipid-siRNA nanoparticles. Synthesis of 2,2-Dilinoleyl-4-dimethylaminoethyl-[1,3]-dioxolane (Lipid A) is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane (Lipid A): 10% DSPC: 40% Cholesterol: 10% PEG-C-DOMG (mole percent) with a particle size of 63.0±20 nm and a 0.027 siRNA/Lipid Ratio.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle. In some embodiments the non-ationic lipid is around from about 7 mol % to about 8 mol %, or 7.0, 7.1, 7.2, 7.3, 7.4, 7.5, 7.6, 7.7, 7.8, 7.9, or 8.0 mol %.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

LNP01

In one embodiment, the lipidoid ND98.4HCl (MW 1487) (Formula 1), Cholesterol (Sigma-Aldrich), and PEG-Ceramide C16 (Avanti Polar Lipids) can be used to prepare lipid-siRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous siRNA (e.g., in sodium acetate pH 5) such that the final ethanol concentration is about 35-45% and the final sodium acetate concentration is about 100-300 mM. Lipid-siRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

| | Cationic Lipid | cationic lipid/non-cationic lipid/cholesterol/ PEG-lipid conjugate Lipid:siRNA ratio | Process |
|---|---|---|---|
| LNP07 | 2,2-Dilinoleyl-4-dimethylaminoethyl-[1,3]-dioxolane (LIPID A) | LIPID A/DSPC/Cholesterol/ PEG-DMG 60/7.5/31/1.5, lipid:siRNA ~6:1 | In-line mixing |
| LNP08 | 2,2-Dilinoleyl-4-dimethylaminoethyl-[1,3]-dioxolane (LIPID A) | LIPID A/DSPC/Cholesterol/ PEG-DMG 60/7.5/31/1.5, lipid:siRNA ~11:1 | In-line mixing |
| LNP09 | 2,2-Dilinoleyl-4-dimethylaminoethyl-[1,3]-dioxolane (LIPID A) | LIPID A/DSPC/Cholesterol/ PEG-DMG 50/10/38.5/1.5 Lipid:siRNA 10:1 | In-line mixing |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/ Cholesterol/PEG-DMG 50/10/38.5/1.5 Lipid:siRNA 10:1 | In-line mixing |
| LNP11 | (6Z,9Z,28Z,31Z)-heptatriaconta-6,9,28,31-tetraen-19-yl 4-(dimethylamino)butanoate (MC3) | MC-3/DSPC/ Cholesterol/PEG-DMG 50/10/38.5/1.5 Lipid:siRNA 10:1 | In-line mixing |
| LNP12 | 1,1'-(2-(4-(2-((2-(bis(2-hydroxydodecyl)amino)ethyl) (2-hydroxydodecyl)amino)ethyl)piperazin-1-yl)ethylazanediyl)didodecan-2-ol (Tech G1) | Tech G1/DSPC/Cholesterol/ PEG-DMG 50/10/38.5/1.5 Lipid:siRNA 10:1 | In-line mixing |

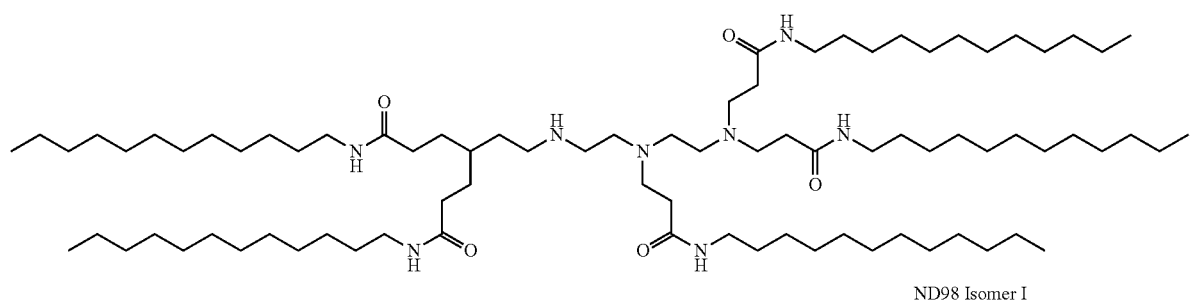

Formula 1

ND98 Isomer I

LNP01 formulations are described, e.g., in International Application Publication No. WO 2008/042973, which is hereby incorporated by reference.

Additional exemplary lipid-siRNA formulations are as follows:

| | Cationic Lipid | cationic lipid/non-cationic lipid/cholesterol/ PEG-lipid conjugate Lipid:siRNA ratio | Process |
|---|---|---|---|
| SNALP | 1,2-Dilinolenyloxy-N,N-dimethylaminopropane (DLinDMA) | DLinDMA/DPPC/ Cholesterol/PEG-cDMA (57.1/7.1/34.4/1.4) lipid:siRNA ~7:1 | |
| SNALP-LIPID A | 2,2-Dilinoleyl-4-dimethylaminoethyl-[1,3]-dioxolane (LIPID A) | LIPID A/DPPC/Cholesterol/ PEG-cDMA 57.1/7.1/34.4/1.4 lipid:siRNA ~7:1 | |
| LNP05 | 2,2-Dilinoleyl-4-dimethylaminoethyl-[1,3]-dioxolane (LIPID A) | LIPID A/DSPC/Cholesterol/ PEG-DMG 57.5/7.5/31.5/3.5 lipid:siRNA ~6:1 | Extrusion |
| LNP06 | 2,2-Dilinoleyl-4-dimethylaminoethyl-[1,3]-dioxolane (LIPID A) | LIPID A/DSPC/Cholesterol/ PEG-DMG 57.5/7.5/31.5/3.5 lipid:siRNA ~11:1 | Extrusion |

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Emulsions

The compositions of the present invention may be prepared and formulated as emulsions. Emulsions are typically heterogenous systems of one liquid dispersed in another in the form of droplets usually exceeding 0.1 µm in diameter (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: non-ionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of dsRNAs and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Penetration Enhancers

In one embodiment, the present invention employs various penetration enhancers to affect the efficient delivery of nucleic acids, particularly dsRNAs, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of dsRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of dsRNAs through the mucosa is enhanced. With regards to their use as penetration enhancers in the present invention, chelating agents have the added advantage of also serving as Dnase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of dsRNAs through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of dsRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

In some embodiments, pharmaceutical compositions featured in the invention include (a) one or more dsRNA compounds and (b) one or more anti-cytokine biologic agents which function by a non-RNAi mechanism. Examples of such biologics include, biologics that target IL1β (e.g., anakinra), IL6 (tocilizumab), or TNF (etanercept, infliximab, adlimumab, or certolizumab).

In some embodiments, pharmaceutical compositions featured in the invention include (a) one or more dsRNA compounds and (b) one or more other chemotherapeutic agents which function by a non-RNAi mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FudR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the dsRNAs featured in the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions featured in the invention. See, generally, The Merck Manual of Diagnosis and Therapy, 15th Ed., Berkow et al., eds., 1987, Rahway, N.J., pages 2499-2506 and 46-49, respectively). Other non-RNAi chemotherapeutic agents are also within the scope of this invention. Two or more combined compounds may be used together or sequentially.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulation a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration, as discussed above, the dsRNAs featured in the invention can be administered in combination with other known agents effective in treatment of pathological processes mediated by SAA expression. In any event, the administering physician can adjust the amount and timing of dsRNA administration on the basis of results observed using standard measures of efficacy known in the art or described herein.

Methods for Treating Diseases Caused by Expression of an SAA Gene

The invention relates in particular to the use of a dsRNA targeting SAA and compositions containing at least one such dsRNA for the treatment of an SAA-mediated disorder or disease. For example, a dsRNA targeting an SAA gene, e.g., one or both of SAA1 and SAA2, can be useful for the treatment of a disorder associated with inflammation, such as arthritis (e.g., rheumatoid arthritis), or tissue injury, reactive (secondary) amyloidosis or systemic amyloidosis, atherosclerosis, or Alzheimer's Disease.

A dsRNA targeting an SAA gene is also used for treatment of symptoms and disorders, such as chronic inflammatory diseases, chronic infections, and neoplasia. Such disorders are frequently associated with amyloidosis. Examples of chronic inflammatory diseases include rheumatoid arthritis, psoriatic arthritis, chronic juvenile arthritis, ankylosing spondylitis, Behcet's syndrome, Reiter's syndrome, Adult Still's disease, inflammatory bowel disease (e.g., Crohn's disease), and hereditary periodic fevers, such as Familial Mediterranean fever. Examples of chronic infections associated with amyloidosis, and suitable for treatment with SAA dsRNAs, include tuberculosis, osteomyelitis, bronchiectasis, leprosy, pyelonephritis, decubitus ulcers, Whipple's disease, acne conglobata, common variable immunodeficiency hypo/agammaglobulinemia, cystic fibrosis. Examples of neoplasia associated with amyloidosis, and suitable for treatment with SAA dsRNAs, include hepatoma, renal carcinoma, Castleman's disease, Hodgkin's disease, Adult hairy cell leukemia, and Waldenstrom's disease.

In one embodiment, a dsRNA targeting an SAA gene is used to treat clinical disorders such as proteinuria/renal insufficiency, diarrhea/obstipation/malabsorption, goiter, neuropathy/carpal tunnel syndrome, hepatomegaly, lymphadenopathy, cardiac. These disorders are frequently present in patients with amyloidosis.

A dsRNA targeting an SAA gene can also be used to treat a proliferative disorder, such as cancer, such as colon cancer. A composition containing a dsRNA targeting an SAA gene is also used to treat a carcinoma of the breast, ovary, cervix, kidney, or a squamous cell.

A composition containing a dsRNA targeting SAA, e.g., one or both of SAA1 or SAA2, may also be used to treat other tumors and cancers, such as breast cancer, lung cancer, head and neck cancer, brain cancer, abdominal cancer, colon cancer, colorectal cancer, esophagus cancer, gastrointestinal cancer, tongue cancer, neuroblastoma, osteosarcoma, ovarian cancer, pancreatic cancer, prostate cancer, cervical cancer (e.g., squamous carcinoma of the cervix), lymphoid tumor, retinoblastoma, Wilm's tumor, multiple myeloma and for the treatment of skin cancer, like melanoma, for the treatment of lymphomas and blood cancer. The compositions featured herein can be used to treat a tumor of the brain or spine.

A dsRNA targeting SAA may be used to treat a proliferative disorder or differentiative disorder. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including those of prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplastic cells of hematopoictic origin, e.g., arising from myeloid, lymphoid or erythroid lineages, or precursor cells thereof.

Owing to the inhibitory effects on SAA expression, a composition according to the invention or a pharmaceutical composition prepared therefrom can enhance the quality of life.

The invention further relates to the use of a dsRNA or a pharmaceutical composition thereof, e.g., for treating an amyloidosis, in combination with other pharmaceuticals and/or other therapeutic methods, e.g., with known pharmaceuticals and/or known therapeutic methods, such as, for example, those which are currently employed for treating this disorders. In one example, a dsRNA targeting SAA can be administered in combination with an anti-cytokine agent such as an anti-IL1β agent (e.g., anakinra), IL6 agent (e.g., tocilizumab), or TNFα agent (e.g., etanercept, infliximab, adlimumab, or certolizumab). In other examples, a dsRNA targeting SAA can be administered in combination with rituxan (rituximab), Eprodisate (Neurochem, Canada). In yet other examples, a dsRNA targeting SAA can be administered in combination with steroids or methotrexate, e.g., to manage chronic inflammatory arthritis. In other examples, a dsRNA targeting SAA can be administered in combination with diuretics, ACE inhibitors, or ARBs, e.g., for management of renal function.

The invention further relates to the use of a dsRNA or a pharmaceutical composition thereof, e.g., for treating a cancer, in combination with other pharmaceuticals and/or other therapeutic methods, e.g., with known pharmaceuticals and/or known therapeutic methods, such as, for example, those which are currently employed for treating these disorders. In one example, administration of a dsRNA targeting SAA can be administered in combination with a chemotherapeutic agent, such as temozolomide, deoxycoformycin, cisplatin, cyclophosphamide, 5-fluorouracil, adriamycin, daunorubicin, tamoxifen aunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FudR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the dsRNAs featured in the invention, such chemotherapeutic agents may be used individually, sequentially (e.g., dsRNA for a period of time, followed by chemotherapy), or in combination with one or more other such agents (e.g., chemotherapy and dsRNA). Two or more combined compounds may be used together or sequentially.

The dsRNA and an additional therapeutic agent can be administered in the same combination, e.g., parenterally, or the additional therapeutic agent can be administered as part of a separate composition or by another method described herein.

Treatment with a dsRNA targeting SAA can also be performed in combination with radiation therapy, such as for treatment of a cancer, such as colon cancer or a carcinoma. A dsRNA featured herein may be administered before or after a surgical procedure to treat a cancer (e.g., to remove a tumor, or a malignant cell or cell mass).

The invention features a method of administering a dsRNA targeting SAA to a patient having a disease or disorder mediated by SAA expression, such as AA amyloidosis. Administration of the dsRNA can stabilize and improve renal function, for example, in a patient with AA amyloidosis. Patients can be administered a therapeutic amount of dsRNA, such as 0.5 mg/kg, 1.0 mg/kg, 1.5 mg/kg, 2.0 mg/kg, or 2.5 mg/kg dsRNA. The dsRNA can be administered by intravenous infusion over a period of time, such as over a 5 minute, 10 minute, 15 minute, 20 minute, or 25 minute period. The administration is repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the dsRNA can reduce serum SAA levels in the patient by at least 20%, 25%, 30%, 40%, 50%, 60%, 70%, 80% or 90%.

Before administration of a full dose of the dsRNA, patients can be administered a smaller dose, such as a 5% infusion reaction, and monitored for adverse effects, such as an allergic reaction or a change in liver function. For example, in patients monitored for changes in liver function, a low incidence of LFT (Liver Function Test) change (e.g., a 10-20% incidence of LFT) is acceptable (e.g., a reversible, 3-fold increase in ALT (alanine aminotransferase) and/or AST (aspartate aminotransferase) levels).

Methods for Inhibiting Expression of an SAA Gene

In yet another aspect, the invention provides a method for inhibiting the expression of an SAA gene in a mammal. The method includes administering a composition featured in the invention to the mammal such that expression of the target SAA gene (e.g., one or both of SAA1 and SAA2) is silenced.

When the organism to be treated is a mammal such as a human, the composition may be administered by any means known in the art including, but not limited to oral or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the dsRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1. dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs are produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides are generated by solid phase synthesis employing the corresponding phosphoramidites and 2'-O-methyl phosphoramidites, respectively (Proligo Biochemie GmbH, Hamburg, Germany). These building blocks are incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages are introduced by replacement of the iodine oxidizer solution with a solution of the Beaucage reagent (Chruachem Ltd, Glasgow, UK) in acetonitrile (1%). Further ancillary reagents are obtained from Mallinckrodt Baker (Griesheim, Germany).

Deprotection and purification of the crude oligoribonucleotides by anion exchange HPLC are carried out according to established procedures. Yields and concentrations are determined by UV absorption of a solution of the respective RNA at a wavelength of 260 nm using a spectral photometer (DU 640B, Beckman Coulter GmbH, UnterschleiBheim, Germany). Double stranded RNA is generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution is stored at −20° C. until use.

For the synthesis of 3'-cholesterol-conjugated siRNAs (herein referred to as -Chol-3'), an appropriately modified solid support is used for RNA synthesis. The modified solid support is prepared as follows:

Diethyl-2-azabutane-1,4-dicarboxylate AA

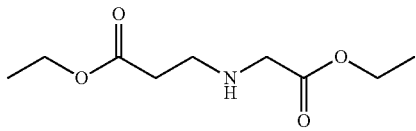

AA

A 4.7 M aqueous solution of sodium hydroxide (50 mL) is added into a stirred, ice-cooled solution of ethyl glycinate hydrochloride (32.19 g, 0.23 mole) in water (50 mL). Then, ethyl acrylate (23.1 g, 0.23 mole) is added and the mixture is stirred at room temperature until completion of the reaction is ascertained by TLC. After 19 h the solution is partitioned with dichloromethane (3×100 mL). The organic layer is dried with anhydrous sodium sulfate, filtered and evaporated. The residue is distilled to afford AA (28.8 g, 61%).

3-{Ethoxycarbonylmethyl-[6-(9H-fluoren-9-yl-methoxycarbonyl-amino)-hexanoyl]-amino}-propionic Acid Ethyl Ester AB

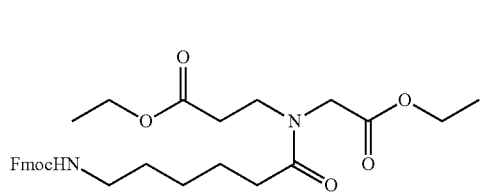

AB

Fmoc-6-amino-hexanoic acid (9.12 g, 25.83 mmol) is dissolved in dichloromethane (50 mL) and cooled with ice. Diisopropylcarbodiimde (3.25 g, 3.99 mL, 25.83 mmol) is added to the solution at 0° C. It is then followed by the addition of Diethyl-azabutane-1,4-dicarboxylate (5 g, 24.6 mmol) and dimethylamino pyridine (0.305 g, 2.5 mmol). The solution is brought to room temperature and stirred further for 6 h. Completion of the reaction is ascertained by TLC. The reaction mixture is concentrated under vacuum and ethyl acetate is added to precipitate diisopropyl urea. The suspension is filtered. The filtrate is washed with 5% aqueous hydrochloric acid, 5% sodium bicarbonate and water. The combined organic layer is dried over sodium sulfate and concentrated to give the crude product which is purified by column chromatography (50% EtOAC/Hexanes) to yield 11.87 g (88%) of AB.

3-[(6-Amino-hexanoyl)-ethoxycarbonylmethyl-amino]-propionic Acid Ethyl Ester AC

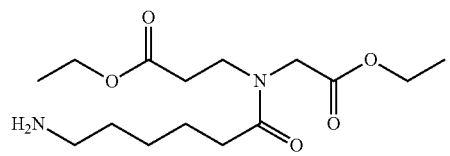

AC

3-{Ethoxycarbonylmethyl-[6-(9H-fluoren-9-ylmethoxy-carbonylamino)-hexanoyl]-amino}-propionic acid ethyl ester AB (11.5 g, 21.3 mmol) is dissolved in 20% piperidine in dimethylformamide at 0° C. The solution is continued stirring for 1 h. The reaction mixture is concentrated under vacuum, water is added to the residue, and the product is extracted with ethyl acetate. The crude product is purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic Acid Ethyl Ester AD

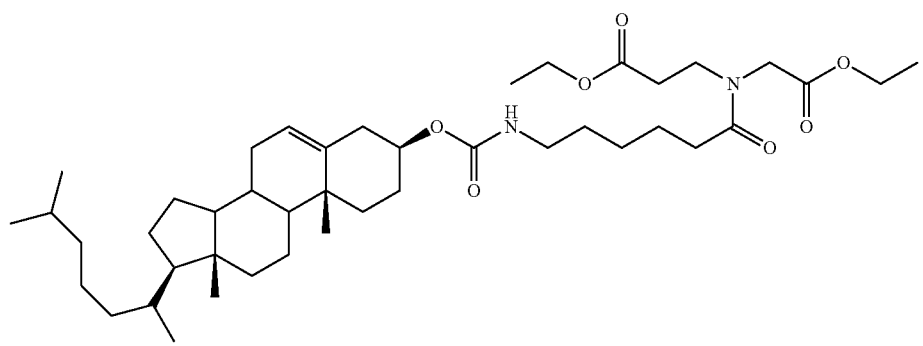

AD

The hydrochloride salt of 3-[(6-Amino-hexanoyl)-ethoxycarbonylmethyl-amino]-propionic acid ethyl ester AC (4.7 g, 14.8 mmol) is taken up in dichloromethane. The suspension is cooled to 0° C. on ice. To the suspension diisopropylethylamine (3.87 g, 5.2 mL, 30 mmol) is added. To the resulting solution cholesteryl chloroformate (6.675 g, 14.8 mmol) is added. The reaction mixture is stirred overnight. The reaction mixture is diluted with dichloromethane and washed with 10% hydrochloric acid. The product is purified by flash chromatography (10.3 g, 92%).

1-{6-[17-(1,5-Dimethyl-hexyl)-10,13-dimethyl-2,3,4,7,8,9,10,11,12,13,14,15,16,17-tetradecahydro-1H-cyclopenta[a] phenanthren-3-yloxycarbonylamino]-hexanoyl}-4-oxo-pyrrolidine-3-carboxylic Acid Ethyl Ester AE

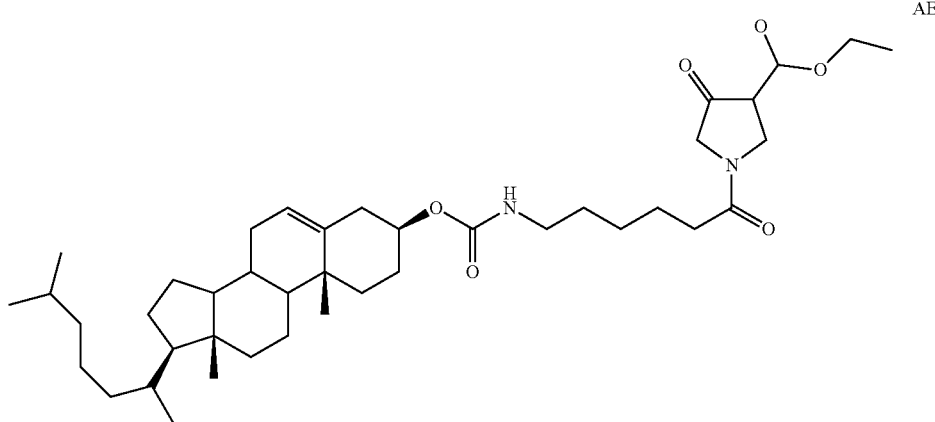 [SMILES: CCOC(O)C1CN(C(=O)CCCCCNC(=O)O[C@H]2CC[C@@]3(C)C(=CCC4C3CC[C@@]3(C)C4CC[C@@H]3C(C)CCCC(C)C)C2)CC1=O]

Potassium t-butoxide (1.1 g, 9.8 mmol) was slurried in 30 mL of dry toluene. The mixture is cooled to 0° C. on ice and 5 g (6.6 mmol) of diester AD is added slowly with stirring within 20 mins. The temperature is kept below 5° C. during the addition. The stirring is continued for 30 mins at 0° C. and 1 mL of glacial acetic acid is added, immediately followed by 4 g of $NaH_2PO_4 \cdot H_2O$ in 40 mL of water The resultant mixture is extracted twice with 100 mL of dichloromethane each and the combined organic extracts are washed twice with 10 mL of phosphate buffer each, dried, and evaporated to dryness. The residue is dissolved in 60 mL of toluene, cooled to 0° C. and extracted with three 50 mL portions of cold pH 9.5 carbonate buffer. The aqueous extracts are adjusted to pH 3 with phosphoric acid, and extracted with five 40 mL portions of chloroform which are combined, dried and evaporated to dryness. The residue is purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic Acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl Ester AF

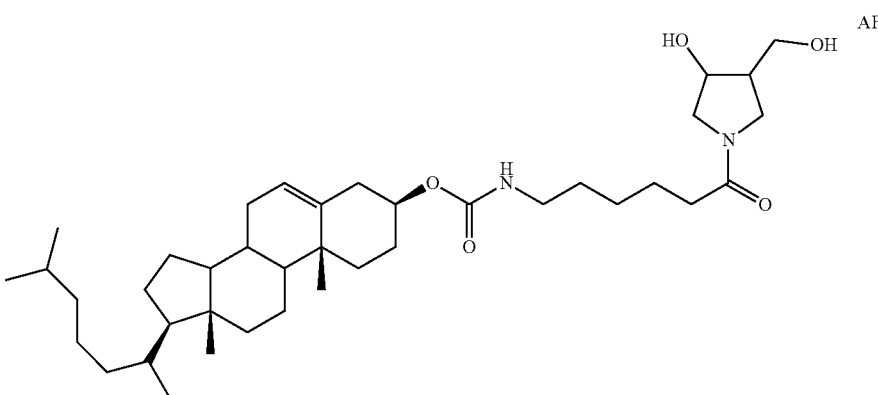 [SMILES: CC(C)CCCC(C)[C@H]1CCC2C3CC=C4C[C@@H](OC(=O)NCCCCCC(=O)N5CC(O)C(CO)C5)CC[C@]4(C)C3CC[C@@]21C]

Methanol (2 mL) is added drop wise over a period of 1 h to a refluxing mixture of b-ketoester AE (1.5 g, 2.2 mmol) and sodium borohydride (0.226 g, 6 mmol) in tetrahydrofuran (10 mL). Stirring is continued at reflux temperature for 1 h. After cooling to room temperature, 1 N HCl (12.5 mL) is added, the mixture is extracted with ethylacetate (3×40 mL). The combined ethylacetate layer is dried over anhydrous sodium sulfate and concentrated under vacuum to yield the product which is purified by column chromatography (10% $MeOH/CHCl_3$) (89%).-

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl Ester AG

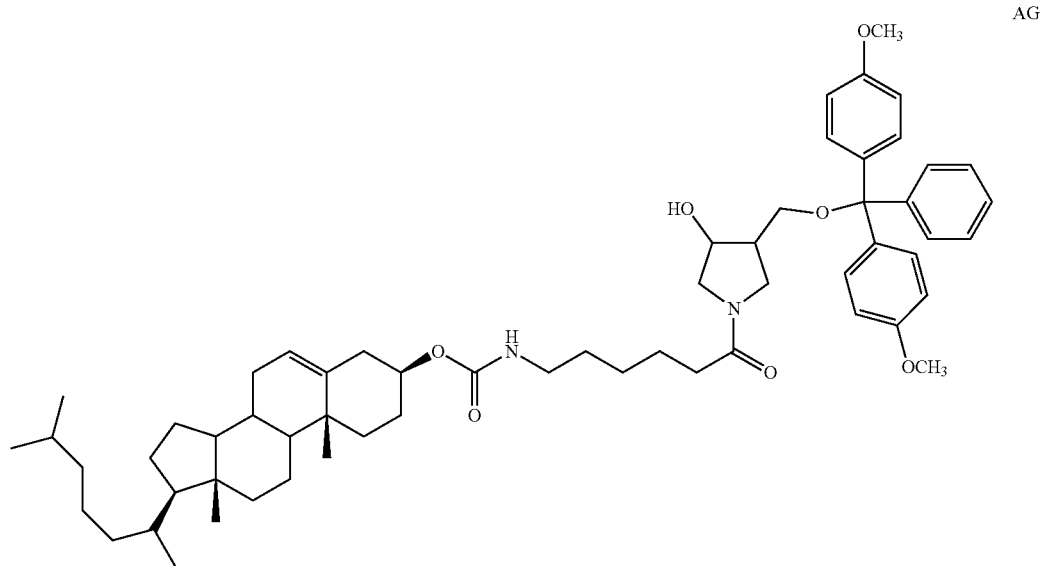 [SMILES: COc1ccc(C(OCC2CN(C(=O)CCCCCNC(=O)O[C@H]3CC[C@@]4(C)C(=CCC5C4CC[C@@]4(C)C5CC[C@@H]4C(C)CCCC(C)C)C3)CC2O)(c2ccccc2)c2ccc(OC)cc2)cc1]

Diol AF (1.25 gm 1.994 mmol) is dried by evaporating with pyridine (2×5 mL) in vacuo. Anhydrous pyridine (10 mL) and 4,4'-dimethoxytritylchloride (0.724 g, 2.13 mmol) are added with stirring. The reaction is carried out at room temperature overnight. The reaction is quenched by the addition of methanol. The reaction mixture is concentrated under vacuum and to the residue dichloromethane (50 mL) is added. The organic layer is washed with 1M aqueous sodium bicarbonate. The organic layer is dried over anhydrous sodium sulfate, filtered and concentrated. The residual pyridine is removed by evaporating with toluene. The crude product is purified by column chromatography (2% MeOH/Chloroform, Rf=0.5 in 5% MeOH/CHCl₃) (1.75 g, 95%).

Succinic acid mono-(4-[bis-(4-methoxy-phenyl)-phenyl-methoxymethyl]-1-{6-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-pyrrolidin-3-yl) Ester AH

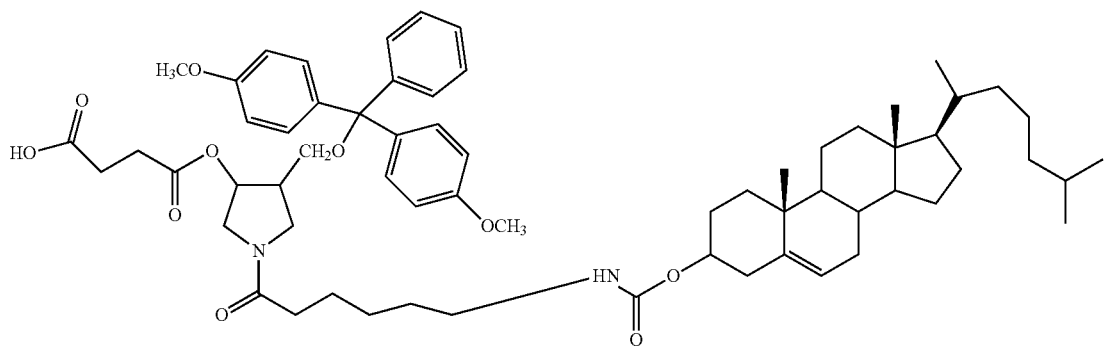

Compound AG (1.0 g, 1.05 mmol) is mixed with succinic anhydride (0.150 g, 1.5 mmol) and DMAP (0.073 g, 0.6 mmol) and dried in a vacuum at 40° C. overnight. The mixture is dissolved in anhydrous dichloroethane (3 mL), triethylamine (0.318 g, 0.440 mL, 3.15 mmol) is added and the solution is stirred at room temperature under argon atmosphere for 16 h. It is then diluted with dichloromethane (40 mL) and washed with ice cold aqueous citric acid (5 wt %, 30 mL) and water (2×20 mL). The organic phase is dried over anhydrous sodium sulfate and concentrated to dryness. The residue is used as such for the next step.

Cholesterol Derivatized CPG AI

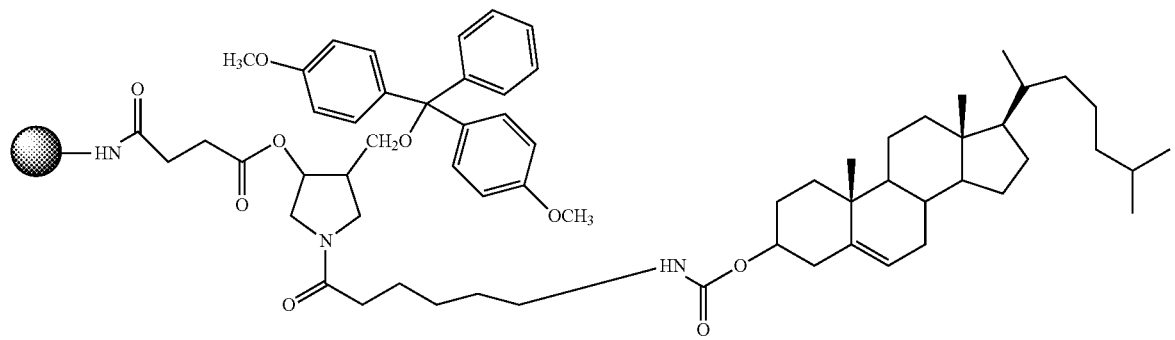

Succinate AH (0.254 g, 0.242 mmol) is dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) are added successively. To the resulting solution triphenylphosphine (0.064 g, 0.242 mmol) in acetonitrile (0.6 ml) is added. The reaction mixture turned bright orange in color. The solution is agitated briefly using a wrist-action shaker (5 mins). Long chain alkyl amine-CPG (LCAA-CPG) (1.5 g, 61 mM) is added. The suspension is agitated for 2 h. The CPG is filtered through a sintered funnel and washed with acetonitrile, dichloromethane and ether successively. Unreacted amino groups are masked using acetic anhydride/pyridine. The achieved loading of the CPG is measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") is performed as described in WO 2004/065601, except that, for the cholesteryl derivative, the oxidation step is performed using the Beaucage reagent in order to introduce a phosphorothioate linkage at the 5'-end of the nucleic acid oligomer.

Nucleic acid sequences are represented below using standard nomenclature, and specifically the abbreviations of Table 1.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
| --- | --- |
| A | adenosine-5'-phosphate |
| C | cytidine-5'-phosphate |
| G | guanosine-5'-phosphate |
| T, dT | 2'-deoxy-thymidine-5'-phosphate |
| U | uridine-5'-phosphate |
| N | any nucleotide (G, A, C, or T) |
| a | 2'-O-methyladenosine-5'-phosphate |
| c | 2'-O-methylcytidine-5'-phosphate |
| g | 2'-O-methylguanosine-5'-phosphate |
| u | 2'-O-methyluridine-5'-phosphate |
| sT, sdT | 2'-deoxy-thymidine-5'phosphate-phosphorothioate |

Example 2. siRNA Design siRNA design was carried out to identify siRNAs targeting SAA1 and SAA2. The design used the SAA1 transcript NM_000331.3 (human), NM_009117.3 (mouse), and the single, near full length, SAA-like trace from cynomolgus monkey, the cDNA sequence Mfa # S27795076 (*Macaca fascicularis*). The SAA2 transcripts used in designing the siRNAs included NM_030754.2 (human) and NM_011314.1 (mouse).

siRNA duplexes were designed with 100% identity to both SAA1 and SAA2 genes. Several sets cross-reactive with human and mouse, human and cynomolgus monkey and human-cynomolgus monkey were designed.

All possible 19mers were created from each sequence. Human-mouse, human-cynomolgus monkey, and human-cynomolgus monkey-mouse subsets were created by searching for identical 19mers from each species using the Python script polyFastaToNmer.py. There were 254 human sense 19mer siRNAs. Of these 254, there were 21 with 100% identity to the human and mouse transcripts; 78 had 100% identity in human and cynomolgus monkey, and two had 100% identity in the three species (human, cynomolgus monkey, and mouse).

The predicted specificity of each siRNA design was used as a criterion for final selection. The SAA siRNAs were used in a comprehensive search against the mouse, human and cynomolgus transcriptomes using the FASTA algorithm. A Python script was then used to parse the alignments and generate a score based on the position and number of mismatches between the siRNA and any potential 'off-target' transcript. The score is weighted to emphasize differences in the 'seed' region of siRNAs, in positions 2-9 from the 5' end of the molecule. Both siRNAs strands were assigned to a category of specificity according to the calculated scores: a score above 3 qualifies as highly specific, equal to 3 as specific and between 2.2 and 2.8 as moderate specific.

Approximately 500-700 19-mer SAA siRNAs were designed and analyzed for SAA isoform/species cross-reactivity and off-target prediction. 78 dsRNAs were selected for further analysis. These 78 siRNAs were predicted to target both SAA1 and SAA2 (hereafter called "SAA" or "SAA1/2"). All 78 sense and antisense human-cynomolgus monkey-specific siRNAs were synthesized with internal 2'Ome modifications and formed into duplexes.

Example 3. In Vitro Efficacy Screening of Serum Amyloid A (SAA)

The 78 SAA siRNAs with 2'OM endo light modifications were screened for efficacy in an in vitro model. SAA-siRNA were reverse transfected at a concentration of 20 nM in Hep3B cells using LF-Max. 24 h later, SAA was induced by adding combined IL-1β and IL6 cytokines. 18 h post-induction, SAA siRNA activity was analyzed by measuring the mRNA level by bDNA 2.0 and TaqMan assays. Protein levels were measured using ELISA assays. The results, shown in Table 3, are from two biologicals, and two technical repeats.

Material and Methods:
Cell Culture:
Hep3B Cells (HB-8064™) were maintained at 37° C., 5% $CO_2$ in Eagle's Minimum Essential Medium (EMEM-GIBCO) with 10% FBS (Omega Scientific Cat # FB02) 1% Antibiotics/Antibiotics Cat #15240-062).

For stock culture, cells should be 90-100% confluent before splitting. Cells are washed and trypsinized with 3 ml 0.25% Trypsin-EDTA and incubated at 37° C., 5% $CO_2$. 7 ml of DMEM 10% FBS 1% Antibiotics/Antimicotics are added and the cells resuspended thoroughly. Appropriate aliquots of cells are added to a new flask containing 30 ml of fresh DMEM 10% FBS 1% Antibiotics/Antimicotics to obtain 90-100% confluence on the desired day. Cells are resuspended and incubated at 37° C., 5% $CO_2$.

Reverse Transfection Using Lipofectamine RNAiMAX.
Lipofectamine™ RNAiMAX No. 13778-150 (1.5 ml size) was stored at +4° C., as suggested by the manufacturer.

Opti-MEM® I Reduced Serum Medium (Cat. No. 31985-062) was used to dilute RNAi duplexes and Lipofectamine™ RNAiMAX before complexing.

BLOCK-IT™ Alexa Fluor® Red Fluorescent Oligo (Cat. No. 14750-100) was used for assessing transfection efficiency.

The Reverse Transfection procedure was used to transfect siRNA into Hep3B cells in a 96-well format. In reverse transfections, the complexes were prepared inside the wells, after which cells suspension was added. For each well to be transfected, RNAi duplex-Lipofectamine RNAiMAX complexes were prepared as follows:

2 ul siRNA duplex (from 20 uM stock) were diluted in 198 μl Opti-MEM® in each well of the dilution plate to have 20 nM final conc. For one dose screening. For IC50 determinations, further dilutions were conducted by mix gently the previous dill and dilute 5 fold serially (40 ul from the 1st dill+160 ul OPT-MEM) to reach a range of 20 nM-50 fM final RNA conc. 10 ul/well siRNA dilution was transferred to the culture plate.

Lipofectamine™ RNAi MAX was mixed gently, then 20 ul Lipofectamine™ RNAi MAX was added to 10 ml Opt-MEM (0.2 μl Lipofectamine™/Well). 10 ul of the mixture was added to each well in the culture plate. The solution was mixed gently and incubated for 10-20 minutes at RT (20 ul lipoplex/well).

The cells were split, counted and diluted in complete growth medium without antibiotics so that 80 μl contained the appropriate number of cells ($2 \times 10^4$/well) to give 30-50% confluence 24 hours after plating.

80 μl of the diluted cells were added to each well with RNAi duplex—Lipofectamine™ RNAiMAX complexes. This gave a final volume of 100 μl and a final RNA concentration of 20 nM (for the single dose assay) and 20 nM-50 fM (IC50 assay). The cells were mixed gently by rocking the plate back and forth. The cells were incubated overnight at 37° C. in a CO2 incubator.

Human SAA induction in Hep-3B using Cytokines (IL-1β+IL-6).

500 ul deionized water was added to a vial of recombinant human IL-1β ((rIL-1β, Thermo Scientific), ED50 or 1 unit of activity=3 pg/ml) to prepare a working stock solution.

This dilution resulted in 20000000 pg/500 ul=13333333 units total in 500 ul, and lul stock solution=26666 units 500 ul deionized water was added to a vial of Recombinant human IL-6 (RIL-61, Thermo Scientific, ED50 or 1 unit of activity=52.5 pg/ml) to prepare a working stock solution. This dilution resulted in 20000000 pg/500 ul=760456.3 units total in 500 ul, and a lul stock solution=1521 units.

Growth media with antibiotics was prepared in a volume sufficient for use in the assay plates, where each well received 100 ul of the media.

For each 4 ml media, 1.2 ul (800 units/well) IL-1β working stock solution and 0.6 ul (23 units/well) IL-6 working stock solution was added, and the solution was mixed well.

The media was removed from each plate and 100 ul of induction media was added.

Some plates were incubated for 16-18 h at 37 C, 5% $CO_2$ to for use in the bDNA and TaqMan assays, and other plates were incubated for 44-46 h for use in the ELISA assays.

Figure 1B:
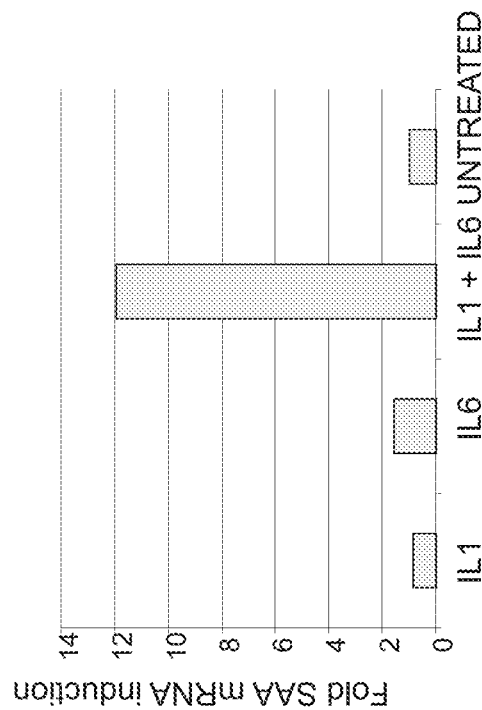
FIG. 1B is a graph showing the effect of IL-1β and IL-6 cytokines on SAA mRNA and protein levels in HepB3 cell culture.

FIGS. 1A and 1B show that SAA can be detected on both mRNA and protein levels. The combination of IL-1β and IL-6 caused a 12-14 fold increase in SAA mRNA levels after 16-18 hours, as measured by TaqMan assay, and caused an 8-fold increase in SAA protein levels after 44 hours, as measured by ELISA.

Human SAA-bDNA Assay Using QuantiGene 2.0 Reagent System (Panomics).

The QuantiGene 2.0 bDNA assay was used to measure SAA RNA levels. All bDNA probe sets were from Panomics. Human specific SAA probe sets were designed to detect both SAA-1 and SAA2 transcripts. Human GAPDH was used as a control housekeeping gene, and the QuantiGene Kit (Panomics) was used to run the assay.

$1^{st}$ bDNA Day.

A fresh lysis mixture (Panomics) dilution was prepared by re-dissolving any precipitates by incubating the mixture at 37° C. followed by gentle swirling. A 1:2 dilution was then prepared (1 volume of Lysis mixture plus 2 volumes nuclease-free water). 10 ul/mL proteinase K (Panomics) was then added to the dilution.

Cells were lysed 18 h post induction to release the target RNA by first removing the supernatant from the cells, then adding 200 ul diluted lysis mixture plus Proteinase K. The plates were sealed with aluminum tape and incubated 30-40 min at 55 C.

To capture target RNA from the cultured cells, plates were removed from 4° C. storage and placed on the bench top to warm completely to room temperature. The sealed foil pouch was removed from the capture plate and 80 ul/well cell lysate was prepared for SAA analysis wells, while 80 ul/well of 1:20 diluted lysate (in diluted lysis mixure 1:2) was prepared for GAPDH analysis.

A working probe mix was prepared for SAA analysis and for GAPDH analysis in separate tubes (1.626 ul nuclease free $H_2O$+887 ul lysis Mixture+134 ul Blocking+40 ul 2.0 probe set=2.688 ul/plate). 20 ul/well of the working probe mix was added, and the plates were sealed very tightly. The plates were incubated at 55 C overnight for hybridization.

$2^{nd}$ bDNA Day.

1× wash buffer was prepared by adding 1.5 mL Wash Buffer Component 1 and 2.5 mL Wash Buffer Component 2, to 496 mL nuclease-free water.

2.0 Pre-Amplifier working reagent was prepared by thawing 2.0 Pre-Amplifier, and centrifuging briefly to collect the contents at the bottom of the tube. 11 μL of the 2.0 Pre-Amplifier was added to 11 mL of Amplifier/Label Probe Diluent and the solution was inverted to mix. The solution was kept at room temperature until use.

2.0 Amplifier working reagent was prepared by thawing 2.0 Amplifier and then centrifuging briefly to collect the contents at the bottom of the tube. 11 μL of 2.0 Amplifier was added to 11 mL of Amplifier/Label Probe Diluent and the solution was inverted to mix. This reagent was also kept at room temperature until ready for use.

2.0 Label Probe Working reagent was prepared by thawing 2.0 Label Probe, then centrifuge briefly to collect the contents at the bottom of the tube. 11 μL of 2.0 Label Probe was added to 11 mL of Amplifier/Label Probe Diluent and the solution was inverted to mix. This solution was also kept at room temperature until ready for use.

The 2.0 substrate was removed from storage at 4 C and allowed to warm to room temperature before use.

200 ul/well of 1× Wash Buffer is added to the Capture plate, and the Capture Plate is inverted over an appropriate receptacle and the contents are forcibly expelled. The inverted plate was firmly tapped on a clean paper towel to dry, and the wash was repeated two more times using 300 μL/well of 1× Wash. The plate was centrifuge at 240×g for 1 min at room temperature.

For hybridization of the 2.0 Pre-Amplifier, 100 ul/well Pre-Amplifier Working Reagent was added to the plate, and the plate was sealed tightly. The plate was then incubated at 55 C for 1 h. The plate was washed three times after pre-amplification.

For hybridization of 2.0 Amplifier, Add 100 ul/well Amplifier Working Reagent 100 ul/well was added to the plate. The plate was sealed very tightly and then incubated at 55 C for 1 h. The plate was washed three times after amplification.

For hybridization of the label Probe, 100 ul/well label Probe Working Reagent was added to the plate, and the plate was sealed very tightly. The plate was incubated at 50 C for 1 h. The plate was washed three times after labeling.

For signal detection, 100 ul of 2.0 Substrate was added to each well and the plate was read in the luminometer after 5 to 15 min.

Human SAA-TaqMan Gene Expression Assay (Applied Biosystems). The Taqman assay used to measure SAA-RNA. All Taqman probes used for the Taqman assays were purchased from Applied Biosystems. The ABI 7900 HT and 7000 cyclers were used for processing and reading of assay plates. No RT PCR control should be run to check for any unspecific amplification or DNA contamination of the RNA used for the Reverse Transcription step.

The master mix was prepared by combining 10 μl PCR Gene Expression Master mix (Applied Biosystems, ABI), 6 μl of Nuclease-free Water, 1ul SAA probe designed to detect both SAA1 and SAA2 (Hs00761940_s1, Applied Biosystems) and 1ul from both 18s endogenous control probe and 2 ul RT cDNA/add later for a total 20 ul reaction.

18 μl of the master mix was aliquoted into each well and then 2 μl of cDNA RT product was added and mixed by pipetting up and down. The plate was sealed with AB Optic tape and processed with a Real Time PCR instrument.

Readings were taken on an ABI 7900 HT real time PCR instrument after which data was analyzed and evaluated.

Human SAA-ELISA KIT Assay (Abazyme, LLC Cat # EL10015).

A Human SAA-ELISA assay was used to determine human serum amyloid A (SAA) protein in cell culture supernatant. Kit reagents were allowed to reach room temperature before using. An SAA Standard was reconstituted with 2.0 mL of Calibrator Diluent II (80 ng/ml)., and the solution allowed to sit for at least 15 minutes with gentle agitation prior to making dilutions. The stock solution was used to produce a serial 2-fold dilution series within the range of the assay (2.5 ng/mL to 80 ng/mL). The undiluted SAA Standard served as the high standard (80 ng/mL) and the Calibrator Diluent served as the zero.

Supernatant samples from cells treated with siRNA and SAA induced one day later by IL1b+IL-6 and after 46 post induction were used, and supernates were diluted 1:3.

1× Wash Buffer (1:19 of distilled or deionized water) was prepared. Substrate A and Substrate B were mixed together in equal volumes 15 minutes before use (need 14 ml total 7 ml each/plate).

To perform the assay, 100 μl of standard or sample were added to the appropriate well of a pre-coated microtiter plate with SAA specific monoclonal antibody. The plate was covered and incubated for 1 hour at room temperature. The plate was washed with 1× wash buffer (350 ul/well) five times. 100 μl of HRP—conjugate—polyclonal antibody specific for SAA was then added to each well. The plate was covered and incubated for one hour at room temperature, and the wash procedure was repeated five times. 100 μL TMB (3,3'5,5' tetramethyl-benzidine) substrate solution was added to each well. The plates were then covered and incubated for 15 minutes at room temperature. An SAA and enzyme-substrate reaction exhibit a change in color.

The enzyme-substrate reaction was terminated by adding 100 μl stop solution (sulphuric acid) to each well and mixing well. The Optical Density (O.D.) at 450±2 nm was measured within 30 minutes using a spectrophotometer (a microtiter plate) reader.

The SAA 2'-Ome duplex RNAs in Table 2 were synthesized; each strand included a phosphate link connecting adjacent 3' dT molecules.

| Symbols used in Table 2 | |
|---|---|
| symbol | definition |
| A | adenosine-3'-phosphate |
| C | cytidine-3'-phosphate |
| G | guanosine-3'-phosphate |
| T | 5-methyluridine-3'-phosphate |
| U | uridine-3'-phosphate |
| c | 2'-O-methylcytidine-3'-phosphate |
| dT | 2'-deoxythymidine-3'-phosphate |
| u | 2'-O-methyluridine-3'-phosphate |

*Target is position of 5' base on transcript of human SAA1 NM_000331.3

Strand: S is sense; AS is antisense

TABLE 2

| Sequences of SAA siRNAs | | | | | | |
|---|---|---|---|---|---|---|
| AD-ID # | Strand | Target* | Sequence without Modifications (5'-3') | SEQ ID NO: | Sequence with Modifications (5'-3') | SEQ ID NO: |
| 18368 | S | 385 | CCAUGCUCGGGGGAACUAU | 157 | ccAuGcucGGGGGAAcuAudTdT | 1 |
|  | AS | 403 | AUAGUUCCCCCGAGCAUGG | 158 | AuAGUUCCCCCGAGcAUGGdTdT | 2 |

TABLE 2-continued

Sequences of SAA siRNAs

| AD-ID # | Strand | Target* | Sequence without Modifications (5'-3') | SEQ ID NO: | Sequence with Modifications (5'-3') | SEQ ID NO: |
|---|---|---|---|---|---|---|
| 18369 | S | 304 | GGCUUUUGAUGGGGCUCGG | 159 | GGcuuuuGAuGGGGcucGGdTdT | 3 |
| | AS | 322 | CCGAGCCCCAUCAAAAGCC | 160 | CCGAGCCCcAUcAAAAGCCdTdT | 4 |
| 18370 | S | 285 | UCUUUUCGUUCCUUGGCGA | 161 | ucuuuucGuuccuuGGcGAdTdT | 5 |
| | AS | 303 | UCGCCAAGGAACGAAAAGA | 162 | UCGCcAAGGAACGAAAAGAdTdT | 6 |
| 18371 | S | 352 | AGAAGCCAAUUACAUCGGC | 163 | AGAAGccAAuuAcAucGGcdTdT | 7 |
| | AS | 370 | GCCGAUGUAAUUGGCUUCU | 164 | GCCGAUGuAAUUGGCUUCUdTdT | 8 |
| 18372 | S | 366 | UCGGCUCAGACAAAUACUU | 165 | ucGGcucAGAcAAAuAcuudTdT | 9 |
| | AS | 384 | AAGUAUUUGUCUGAGCCGA | 166 | AAGuAUUUGUCUGAGCCGAdTdT | 10 |
| 18373 | S | 378 | AAUACUUCCAUGCUCGGGG | 167 | AAuAcuccAuGcucGGGGdTdT | 11 |
| | AS | 396 | CCCCGAGCAUGGAAGUAUU | 168 | CCCCGAGcAUGGAAGuAUUdTdT | 12 |
| 18374 | S | 551 | CCCAAUCACUUCCGACCUG | 169 | cccAAucAcuccGAccuGdTdT | 13 |
| | AS | 569 | AGGUCGGAAGUGAUUGGGTT | 170 | cAGGUCGGAAGUGAUUGGGdTdT | 14 |
| 18375 | S | 277 | CCGAAGCUUCUUUUCGUUC | 171 | ccGAAGcuucuuuucGuucdTdT | 15 |
| | AS | 295 | GAACGAAAAGAAGCUUCGG | 172 | GAACGAAAAGAAGCUUCGGdTdT | 16 |
| 18376 | S | 359 | AAUUACAUCGGCUCAGACA | 173 | AAuuAcAucGGcucAGAcAdTdT | 17 |
| | AS | 377 | UGUCUGAGCCGAUGUAAUU | 174 | UGUCUGAGCCGAUGuAAUUdTdT | 18 |
| 18377 | S | 361 | UUACAUCGGCUCAGACAAA | 175 | uuAcAucGGcucAGAcAAAdTdT | 19 |
| | AS | 379 | UUUGUCUGAGCCGAUGUAA | 176 | UUUGUCUGAGCCGAUGuAAdTdT | 20 |
| 18378 | S | 383 | UUCCAUGCUCGGGGAACU | 177 | uuccAuGcucGGGGGAAcudTdT | 21 |
| | AS | 401 | AGUUCCCCGAGCAUGGAA | 178 | AGUUCCCCGAGcAUGGAAdTdT | 22 |
| 18379 | S | 386 | CAUGCUCGGGGAACUAUG | 179 | cAuGcucGGGGGAAcuAuGdTdT | 23 |
| | AS | 404 | CAUAGUUCCCCGAGCAUG | 180 | cAuAGUUCCCCGAGcAUGdTdT | 24 |
| 18380 | S | 305 | GCUUUUGAUGGGGCUCGG | 181 | GcuuuuGAuGGGGcucGGdTdT | 25 |
| | AS | 323 | CCCGAGCCCCAUCAAAAGC | 182 | CCCGAGCCCcAUcAAAAGCdTdT | 26 |
| 18381 | S | 334 | AGCCUACUCUGACAUGAGA | 183 | AGccuAcucuGAcAuGAGAdTdT | 27 |
| | AS | 352 | UCUCAUGUCAGAGUAGGCU | 184 | UCUcAUGUcAGAGuAGGCUdTdT | 28 |
| 18382 | S | 364 | CAUCGGCUCAGACAAAUAC | 185 | cAucGGcucAGAcAAAuAcdTdT | 29 |
| | AS | 382 | GUAUUUGUCUGAGCCGAUG | 186 | GuAUUUGUCUGAGCCGAUGdTdT | 30 |
| 18383 | S | 547 | AGACCCCAAUCACUUCCGA | 187 | AGAccccAAucAcuuccGAdTdT | 31 |
| | AS | 565 | UCGGAAGUGAUUGGGGUCU | 188 | UCGGAAGUGAUUGGGGUCUdTdT | 32 |
| 18384 | S | 579 | CUGAGAAAUACUGAGCUUC | 189 | cuGAGAAAuAcuGAGcuucdTdT | 33 |
| | AS | 597 | GAAGCUCAGUAUUUCUCAG | 190 | GAAGCUcAGuAUUUCUcAGdTdT | 34 |
| 18385 | S | 275 | AGCCGAAGCUUCUUUUCGU | 191 | AGccGAAGcuucuuuucGudTdT | 35 |
| | AS | 293 | ACGAAAAGAAGCUUCGGCU | 192 | ACGAAAAGAAGCUUCGGCUdTdT | 36 |
| 18386 | S | 286 | CUUUUCGUUCCUUGGCGAG | 193 | cuuuucGuuccuuGGcGAGdTdT | 37 |
| | AS | 304 | CUCGCCAAGGAACGAAAAG | 194 | CUCGCcAAGGAACGAAAAGdTdT | 38 |
| 18387 | S | 287 | UUUUCGUUCCUUGGCGAGG | 195 | uuuucGuuccuuGGcGAGGdTdT | 39 |
| | AS | 305 | CCUCGCCAAGGAACGAAAA | 196 | CCUCGCcAAGGAACGAAAAdTdT | 40 |
| 18388 | S | 357 | CCAAUUACAUCGGCUCAGA | 197 | ccAAuuAcAucGGcucAGAdTdT | 41 |
| | AS | 375 | UCUGAGCCGAUGUAAUUGG | 198 | UCUGAGCCGAUGuAAUUGGdTdT | 42 |
| 18389 | S | 358 | CAAUUACAUCGGCUCAGAC | 199 | cAAuuAcAucGGcucAGAcdTdT | 43 |
| | AS | 376 | GUCUGAGCCGAUGUAAUUG | 200 | GUCUGAGCCGAUGuAAUUGdTdT | 44 |
| 18390 | S | 299 | GGCGAGGCUUUUGAUGGGG | 201 | GGcGAGGcuuuuGAuGGGGdTdT | 45 |
| | AS | 317 | CCCCAUCAAAAGCCUCGCC | 202 | CCCcAUcAAAAGCCUCGCCdTdT | 46 |
| 18391 | S | 316 | GGCUCGGGACAUGUGGAGA | 203 | GGcucGGGAcAuGuGGAGAdTdT | 47 |
| | AS | 334 | UCUCCACAUGUCCCGAGCC | 204 | UCUCcAcAUGUCCCGAGCCdTdT | 48 |
| 18392 | S | 345 | ACAUGAGAGAAGCCAAUUA | 205 | AcAuGAGAGAAGccAAuuAdTdT | 49 |
| | AS | 363 | UAAUUGGCUUCUCUCAUGU | 206 | uAAUUGGCUUCUCUcAUGUdTdT | 50 |
| 18393 | S | 346 | CAUGAGAGAAGCCAAUUAC | 207 | cAuGAGAGAAGccAAuuAcdTdT | 51 |
| | AS | 364 | GUAAUUGGCUUCUCUCAUG | 208 | GuAAUUGGCUUCUCUcAUGdTdT | 52 |

TABLE 2-continued

Sequences of SAA siRNAs

| AD-ID # | Strand | Target* | Sequence without Modifications (5'-3') | SEQ ID NO: | Sequence with Modifications (5'-3') | SEQ ID NO: |
|---|---|---|---|---|---|---|
| 18394 | S | 355 | AGCCAAUUACAUCGGCUCA | 209 | AgccAAuuAcAucGGcucAdTdT | 53 |
|  | AS | 373 | UGAGCCGAUGUAAUUGGCU | 210 | UGAGCCGAUGuAAUUGGCUdTdT | 54 |
| 18395 | S | 356 | GCCAAUUACAUCGGCUCAG | 211 | GccAAuuAcAucGGcucAGdTdT | 55 |
|  | AS | 374 | CUGAGCCGAUGUAAUUGGC | 212 | CUGAGCCGAUGuAAUUGGCdTdT | 56 |
| 18396 | S | 367 | CGGCUCAGACAAAUACUUC | 213 | cGGcucAGAcAAAuAcuucdTdT | 57 |
|  | AS | 385 | GAAGUAUUUGUCUGAGCCG | 214 | GAAGuAUUUGUCUGAGCCGdTdT | 58 |
| 18397 | S | 223 | CAUGAAGCUUCUCACGGGC | 215 | cAuGAAGcuucucAcGGGcdTdT | 59 |
|  | AS | 241 | GCCCGUGAGAAGCUUCAUG | 216 | GCCCGUGAGAAGCUUcAUGdTdT | 60 |
| 18398 | S | 485 | GGCCAUGGUGCGGAGGACU | 217 | GGccAuGGuGcGGAGGAcudTdT | 61 |
|  | AS | 503 | AGUCCUCCGCACCAUGGCC | 218 | AGUCCUCCGcAccAUGGCCdTdT | 62 |
| 18399 | S | 548 | GACCCCAAUCACUUCCGAC | 219 | GaccccAAucAcuuccGAcdTdT | 63 |
|  | AS | 566 | GUCGGAAGUGAUUGGGGUC | 220 | GUCGGAAGUGAUUGGGGUCdTdT | 64 |
| 18400 | S | 550 | CCCCAAUCACUUCCGACCU | 221 | ccccAAucAcuuccGAccudTdT | 65 |
|  | AS | 568 | AGGUCGGAAGUGAUUGGGG | 222 | AGGUCGGAAGUGAUUGGGGdTdT | 66 |
| 18401 | S | 573 | GCCUGCCUGAGAAAUACUG | 223 | GccuGccuGAGAAAuAcuGdTdT | 67 |
|  | AS | 591 | CAGUAUUUCUCAGGCAGGC | 224 | cAGuAUUUCUCAGGcAGGCdTdT | 68 |
| 18402 | S | 276 | GCCGAAGCUUCUUUUCGUU | 225 | GccGAAGcuucuuuucGuudTdT | 69 |
|  | AS | 294 | AACGAAAAGAAGCUUCGGC | 226 | AACGAAAAGAAGCUUCGGCdTdT | 70 |
| 18403 | S | 279 | GAAGCUUCUUUUCGUUCCU | 227 | GAAGcuucuuuucGuuccudTdT | 71 |
|  | AS | 297 | AGGAACGAAAAGAAGCUUC | 228 | AGGAACGAAAAGAAGCUUCdTdT | 72 |
| 18404 | S | 280 | AAGCUUCUUUUCGUUCCUU | 229 | AAGcuucuuuucGuuccuudTdT | 73 |
|  | AS | 298 | AAGGAACGAAAAGAAGCUU | 230 | AAGGAACGAAAAGAAGCUUdTdT | 74 |
| 18405 | S | 291 | CGUUCCUUGGCGAGGCUUU | 231 | cGuuccuuGGcGAGGcuuudTdT | 75 |
|  | AS | 309 | AAAGCCUCGCCAAGGAACG | 232 | AAAGCCUCGCcAAGGAACGdTdT | 76 |
| 18406 | S | 292 | GUUCCUUGGCGAGGCUUUU | 233 | GuuccuuGGcGAGGcuuuudTdT | 77 |
|  | AS | 310 | AAAAGCCUCGCCAAGGAAC | 234 | AAAAGCCUCGCcAAGGAACdTdT | 78 |
| 18407 | S | 296 | CUUGGCGAGGCUUUUGAUG | 235 | cuuGGcGAGGcuuuuGAuGdTdT | 79 |
|  | AS | 314 | CAUCAAAAGCCUCGCCAAG | 236 | cAUcAAAAGCCUCGCcAAGdTdT | 80 |
| 18408 | S | 298 | UGGCGAGGCUUUUGAUGGG | 237 | uGGcGAGGcuuuuGAuGGGdTdT | 81 |
|  | AS | 316 | CCCAUCAAAAGCCUCGCCA | 238 | CCcAUcAAAAGCCUCGCcAdTdT | 82 |
| 18409 | S | 340 | CUCUGACAUGAGAGAAGCC | 239 | cucuGAcAuGAGAGAAGccdTdT | 83 |
|  | AS | 358 | GGCUUCUCUCAUGUCAGAG | 240 | GGCUUCUCUcAUGUcAGAGdTdT | 84 |
| 18410 | S | 235 | CACGGGCCUGGUUUUCUGC | 241 | cAcGGGccuGGuuuucuGcdTdT | 85 |
|  | AS | 253 | GCAGAAAACCAGGCCCGUG | 242 | GcAGAAAACcAGGCCCGUGdTdT | 86 |
| 18411 | S | 306 | CUUUUGAUGGGGCUCGGGA | 243 | cuuuuGAuGGGGcucGGGAdTdT | 87 |
|  | AS | 324 | UCCCGAGCCCCAUCAAAAG | 244 | UCCCGAGCCCcAUcAAAAGdTdT | 88 |
| 18412 | S | 297 | UUGGCGAGGCUUUUGAUGG | 245 | uuGGcGAGGcuuuuGAuGGdTdT | 89 |
|  | AS | 315 | CCAUCAAAAGCCUCGCCAA | 246 | CcAUcAAAAGCCUCGCcAAdTdT | 90 |
| 18413 | S | 381 | ACUUCCAUGCUCGGGGAA | 247 | AcuuccAuGcucGGGGAAdTdT | 91 |
|  | AS | 399 | UUCCCCGAGCAUGGAAGU | 248 | UUCCCCGAGcAUGGAAGUdTdT | 92 |
| 18414 | S | 246 | UUUUCUGCUCCUUGGUCCU | 249 | uuuucuGcuccuuGGuccudTdT | 93 |
|  | AS | 264 | AGGACCAAGGAGCAGAAAA | 250 | AGGAccAAGGAGcAGAAAAdTdT | 94 |
| 18415 | S | 230 | CUUCUCACGGGCCUGGUUU | 251 | cuucucAcGGGccuGGuuudTdT | 95 |
|  | AS | 248 | AAACCAGGCCCGUGAGAAG | 252 | AAAccAGGCCCGUGAGAAGdTdT | 96 |
| 18416 | S | 360 | AUUACAUCGGCUCAGACAA | 253 | AuuAcAucGGcucAGAcAAdTdT | 97 |
|  | AS | 378 | UUGUCUGAGCCGAUGUAAU | 254 | UUGUCUGAGCCGAUGuAAUdTdT | 98 |
| 18417 | S | 379 | AUACUUCCAUGCUCGGGGG | 255 | AuAcuccAuGcucGGGGGdTdT | 99 |
|  | AS | 397 | CCCCCGAGCAUGGAAGUAU | 256 | CCCCCGAGcAUGGAAGuAUdTdT | 100 |
| 18418 | S | 300 | GCGAGGCUUUUGAUGGGGC | 257 | GcGAGGcuuuuGAuGGGGcdTdT | 101 |
|  | AS | 318 | GCCCCAUCAAAAGCCUCGC | 258 | GCCCcAUcAAAAGCCUCGCdTdT | 102 |

TABLE 2-continued

Sequences of SAA siRNAs

| AD-ID # | Strand | Target* | Sequence without Modifications (5'-3') | SEQ ID NO: | Sequence with Modifications (5'-3') | SEQ ID NO: |
|---|---|---|---|---|---|---|
| 18419 | S | 317 | GCUCGGGACAUGUGGAGAG | 259 | GcucGGGAcAuGuGGAGAGdTdT | 103 |
|  | AS | 335 | CUCUCCACAUGUCCCGAGC | 260 | CUCUCCAcAUGUCCCGAGCdTdT | 104 |
| 18420 | S | 324 | ACAUGUGGAGAGCCUACUC | 261 | AcAuGuGGAGAGccuAcucdTdT | 105 |
|  | AS | 342 | GAGUAGGCUCUCCACAUGU | 262 | GAGuAGGCUCUCcAcAUGUdTdT | 106 |
| 18421 | S | 384 | UCCAUGCUCGGGGAACUA | 263 | uccAuGcucGGGGGAAcuAdTdT | 107 |
|  | AS | 402 | UAGUUCCCCGAGCAUGGA | 264 | uAGUUCCCCGAGcAUGGAdTdT | 108 |
| 18422 | S | 555 | AUCACUUCCGACCUGCUGG | 265 | AucAcuuccGAccuGcuGGdTdT | 109 |
|  | AS | 573 | CCAGCAGGUCGGAAGUGAU | 266 | CcAGcAGGUCGGAAGUGAUdTdT | 110 |
| 18423 | S | 322 | GGACAUGUGGAGAGCCUAC | 267 | GGAcAuGuGGAGAGccuAcdTdT | 111 |
|  | AS | 340 | GUAGGCUCUCCACAUGUCC | 268 | GuAGGCUCUCcAcAUGUCCdTdT | 112 |
| 18424 | S | 325 | CAUGUGGAGAGCCUACUCU | 269 | cAuGuGGAGAGccuAcucudTdT | 113 |
|  | AS | 343 | AGAGUAGGCUCUCCACAUG | 270 | AGAGuAGGCUCUCcAcAUGdTdT | 114 |
| 18425 | S | 330 | GGAGAGCCUACUCUGACAU | 271 | GGAGAGccuAcucuGAcAudTdT | 115 |
|  | AS | 348 | AUGUCAGAGUAGGCUCUCC | 272 | AUGUcAGAGuAGGCUCUCCdTdT | 116 |
| 18426 | S | 331 | GAGAGCCUACUCUGACAUG | 273 | GAGAGccuAcucuGAcAuGdTdT | 117 |
|  | AS | 349 | CAUGUCAGAGUAGGCUCUC | 274 | cAUGUcAGAGuAGGCUCUCdTdT | 118 |
| 18427 | S | 338 | UACUCUGACAUGAGAGAAG | 275 | uAcucuGAcAuGAGAGAAGdTdT | 119 |
|  | AS | 356 | CUUCUCUCAUGUCAGAGUA | 276 | CUUCUCUcAUGUcAGAGuAdTdT | 120 |
| 18428 | S | 353 | GAAGCCAAUUACAUCGGCU | 277 | GAAGccAAuuAcAucGGcudTdT | 121 |
|  | AS | 371 | AGCCGAUGUAAUUGGCUUC | 278 | AGCCGAUGuAAUUGGCUUCdTdT | 122 |
| 18429 | S | 369 | GCUCAGACAAAUACUUCCA | 279 | GcucAGAcAAAuAcuuccAdTdT | 123 |
|  | AS | 387 | UGGAAGUAUUUGUCUGAGC | 280 | UGGAAGuAUUUGUCUGAGCdTdT | 124 |
| 18430 | S | 380 | UACUUCCAUGCUCGGGGGA | 281 | uAcuccAuGcucGGGGGAdTdT | 125 |
|  | AS | 398 | UCCCCCGAGCAUGGAAGUA | 282 | UCCCCCGAGcAUGGAAGuAdTdT | 126 |
| 18431 | S | 220 | CACCAUGAAGCUUCUCACG | 283 | cAccAuGAAGcuucucAcGdTdT | 127 |
|  | AS | 238 | CGUGAGAAGCUUCAUGGUG | 284 | CGUGAGAAGCUUcAUGGUGdTdT | 128 |
| 18432 | S | 410 | GCCAAAAGGGGACCUGGGG | 285 | GccAAAAGGGGAccuGGGGdTdT | 129 |
|  | AS | 428 | CCCCAGGUCCCCUUUUGGC | 286 | CCCcAGGUCCCCUUUUGGCdTdT | 130 |
| 18433 | S | 224 | AUGAAGCUUCUCACGGGCC | 287 | AuGAAGcuucucAcGGGccdTdT | 131 |
|  | AS | 242 | GGCCCGUGAGAAGCUUCAU | 288 | GGCCCGUGAGAAGCUUcAUdTdT | 132 |
| 18434 | S | 486 | GCCAUGGUGCGGAGGACUC | 289 | GccAuGGuGcGGAGGAcucdTdT | 133 |
|  | AS | 504 | GAGUCCUCCGCACCAUGGC | 290 | GAGUCCUCCGcACcAUGGCdTdT | 134 |
| 18435 | S | 487 | CCAUGGUGCGGAGGACUCG | 291 | ccAuGGuGcGGAGGAcucGdTdT | 135 |
|  | AS | 505 | CGAGUCCUCCGCACCAUGG | 292 | CGAGUCCUCCGcAccAUGGdTdT | 136 |
| 18436 | S | 237 | CGGGCCUGGUUUUCUGCUC | 293 | cGGGccuGGuuuucuGcucdTdT | 137 |
|  | AS | 255 | GAGCAGAAAACCAGGCCCG | 294 | GAGcAGAAAACcAGGCCCGdTdT | 138 |
| 18437 | S | 268 | UGUCAGCAGCCGAAGCUUC | 295 | uGucAGcAGccGAAGcuucdTdT | 139 |
|  | AS | 286 | GAAGCUUCGGCUGCUGACA | 296 | GAAGCUUCGGCUGCUGAcAdTdT | 140 |
| 18438 | S | 273 | GCAGCCGAAGCUUCUUUUC | 297 | GcAGccGAAGcuucuuuucdTdT | 141 |
|  | AS | 291 | GAAAAGAAGCUUCGGCUGC | 298 | GAAAAGAAGCUUCGGCUGCdTdT | 142 |
| 18439 | S | 282 | GCUUCUUUUCGUUCCUUGG | 299 | GcuucuuuucGuuccuuGGdTdT | 143 |
|  | AS | 300 | CCAAGGAACGAAAAGAAGC | 300 | CcAAGGAACGAAAAGAAGCdTdT | 144 |
| 18440 | S | 293 | UUCCUUGGCGAGGCUUUUG | 301 | uuccuuGGcGAGGcuuuuGdTdT | 145 |
|  | AS | 311 | CAAAAGCCUCGCCAAGGAA | 302 | cAAAAGCCUCGCcAAGGAAdTdT | 146 |
| 18441 | S | 294 | UCCUUGGCGAGGCUUUUGA | 303 | uccuuGGcGAGGcuuuuGAdTdT | 147 |
|  | AS | 312 | UCAAAAGCCUCGCCAAGGA | 304 | UcAAAAGCCUCGCcAAGGAdTdT | 148 |
| 18442 | S | 583 | GAAAUACUGAGCUUCCUCU | 305 | GAAAuAcuGAGcuuccucudTdT | 149 |
|  | AS | 601 | AGAGGAAGCUCAGUAUUUC | 306 | AGAGGAAGCUcAGuAUUUCdTdT | 150 |
| 18443 | S | 549 | ACCCCAAUCACUUCCGACC | 307 | AccccAAucAcuuccGAccdTdT | 151 |
|  | AS | 567 | GGUCGGAAGUGAUUGGGGU | 308 | GGUCGGAAGUGAUUGGGGUdTdT | 152 |

TABLE 2-continued

Sequences of SAA siRNAs

| AD-ID # | Strand | Target* | Sequence without Modifications (5'-3') | SEQ ID NO: | Sequence with Modifications (5'-3') | SEQ ID NO: |
|---|---|---|---|---|---|---|
| 18444 | S | 393 | GGGGGAACUAUGAUGCUGC | 309 | GGGGGAAcuAuGAuGcuGcdTdT | 153 |
|  | AS | 411 | GCAGCAUCAUAGUUCCCCC | 310 | GcAGcAUcAuAGUUCCCCCdTdT | 154 |
| 18445 | S | 373 | AGACAAAUACUUCCAUGCU | 311 | AGAcAAAuAcuuccAuGcudTdT | 155 |
|  | AS | 391 | AGCAUGGAAGUAUUUGUCU | 312 | AGcAUGGAAGuAUUUGUCUdTdT | 156 |

TABLE 3

Results from in vitro efficacy screen of SAA siRNAs

| AD-ID# | SAA-siRNA specific/cross-reactive | % SAA activity relative to unspecific control | | |
|---|---|---|---|---|
|  |  | ELISA | bDNA | TaqMan |
| 18406 | Human | 100 | 93 | 97 |
| 18440 | Human | 100 | 92 | 96 |
| 18372 | Human | 100 | 94 | 92 |
| 18402 | Human | 100 | 92 | 94 |
| 18408 | Human | 100 | 91 | 93 |
| 18386 | Human | 100 | 89 | 95 |
| 18390 | Human | 100 | 89 | 95 |
| 18403 | Human | 100 | 88 | 96 |
| 18437 | Human | 94 | 93 | 97 |
| 18376 | Human | 100 | 95 | 87 |
| 18438 | Human | 100 | 90 | 93 |
| 18396 | Human | 100 | 85 | 97 |
| 18370 | Human | 100 | 94 | 85 |
| 18416 | Human | 97 | 92 | 90 |
| 18384 | Human | 100 | 85 | 92 |
| 18409 | Human | 98 | 83 | 89 |
| 18388 | Human | 100 | 80 | 88 |
| 18387 | Human | 96 | 79 | 90 |
| 18427 | Human | 92 | 82 | 90 |
| 18377 | Human | 100 | 68 | 90 |
| 18407 | Human | 91 | 79 | 87 |
| 18385 | Human | 100 | 51 | 97 |
| 18432 | Human | 88 | 76 | 82 |
| 18375 | Human | 100 | 67 | 80 |
| 18429 | Human | 86 | 76 | 82 |
| 18439 | Human | 80 | 69 | 80 |
| 18380 | Human | 98 | 41 | 79 |
| 18381 | Human | 85 | 72 | 66 |
| 18404 | Human | 83 | 64 | 73 |
| 18371 | Human | 65 | 96 | 29 |
| 18442 | Human | 90 | 56 | 60 |
| 18389 | Human | 75 | 86 | 39 |
| 18393 | Human | 73 | 88 | 32 |
| 18401 | Human | 80 | 67 | 58 |
| 18382 | Human | 82 | 70 | 51 |
| 18395 | Human | 63 | 60 | 57 |
| 18405 | Human | 46 | 60 | 58 |
| 18369 | Human | 85 | 43 | 51 |
| 18394 | Human | 0 | 83 | 47 |
| 18392 | Human | 100 | 32 | 0 |
| 18412 | Human | 36 | 52 | 49 |
| 18435 | Human | 41 | 45 | 45 |
| 18398 | Human | 28 | 46 | 46 |
| 18428 | Human | 4 | 27 | 57 |
| 18411 | Human | 17 | 33 | 50 |
| 18441 | Human | 52 | 32 | 9 |
| 18418 | Human | 3 | 15 | 30 |
| 18431 | Human and cyno | 100 | 89 | 97 |
| 18400 | Human and cyno | 100 | 86 | 92 |
| 18420 | Human and cyno | 100 | 87 | 89 |
| 18397 | Human and cyno | 100 | 83 | 92 |
| 18374 | Human and cyno | 99 | 90 | 82 |
| 18415 | Human and cyno | 99 | 83 | 89 |
| 18436 | Human and cyno | 97 | 80 | 85 |
| 18425 | Human and cyno | 92 | 75 | 87 |
| 18399 | Human and cyno | 92 | 75 | 85 |
| 18391 | Human and cyno | 68 | 92 | 75 |
| 18414 | Human and cyno | 86 | 73 | 81 |
| 18443 | Human and cyno | 91 | 74 | 70 |
| 18419 | Human and cyno | 88 | 67 | 80 |
| 18383 | Human and cyno | 63 | 71 | 68 |
| 18410 | Human and cyno | 63 | 49 | 54 |
| 18426 | Human and cyno | 57 | 34 | 55 |
| 18422 | Human and cyno | 16 | 23 | 41 |
| 18424 | Human and cyno | 0 | 24 | 38 |
| 18433 | Human and cyno | 0 | 33 | 20 |
| 18423 | Human and cyno | 0 | 0 | 0 |
| 18417 | Human and mouse | 95 | 77 | 83 |
| 18379 | Human and mouse | 99 | 54 | 89 |
| 18373 | Human and mouse | 96 | 76 | 69 |
| 18368 | Human and mouse | 88 | 79 | 54 |
| 18430 | Human and mouse | 54 | 49 | 72 |
| 18413 | Human and mouse | 28 | 51 | 53 |
| 18421 | Human and mouse | 14 | 49 | 45 |
| 18378 | Human and mouse | 0 | 50 | 20 |
| 18444 | Human, cyno and mouse | 92 | 73 | 76 |
| 18445 | Human, cyno and mouse | 93 | 68 | 74 |

Figure 2:
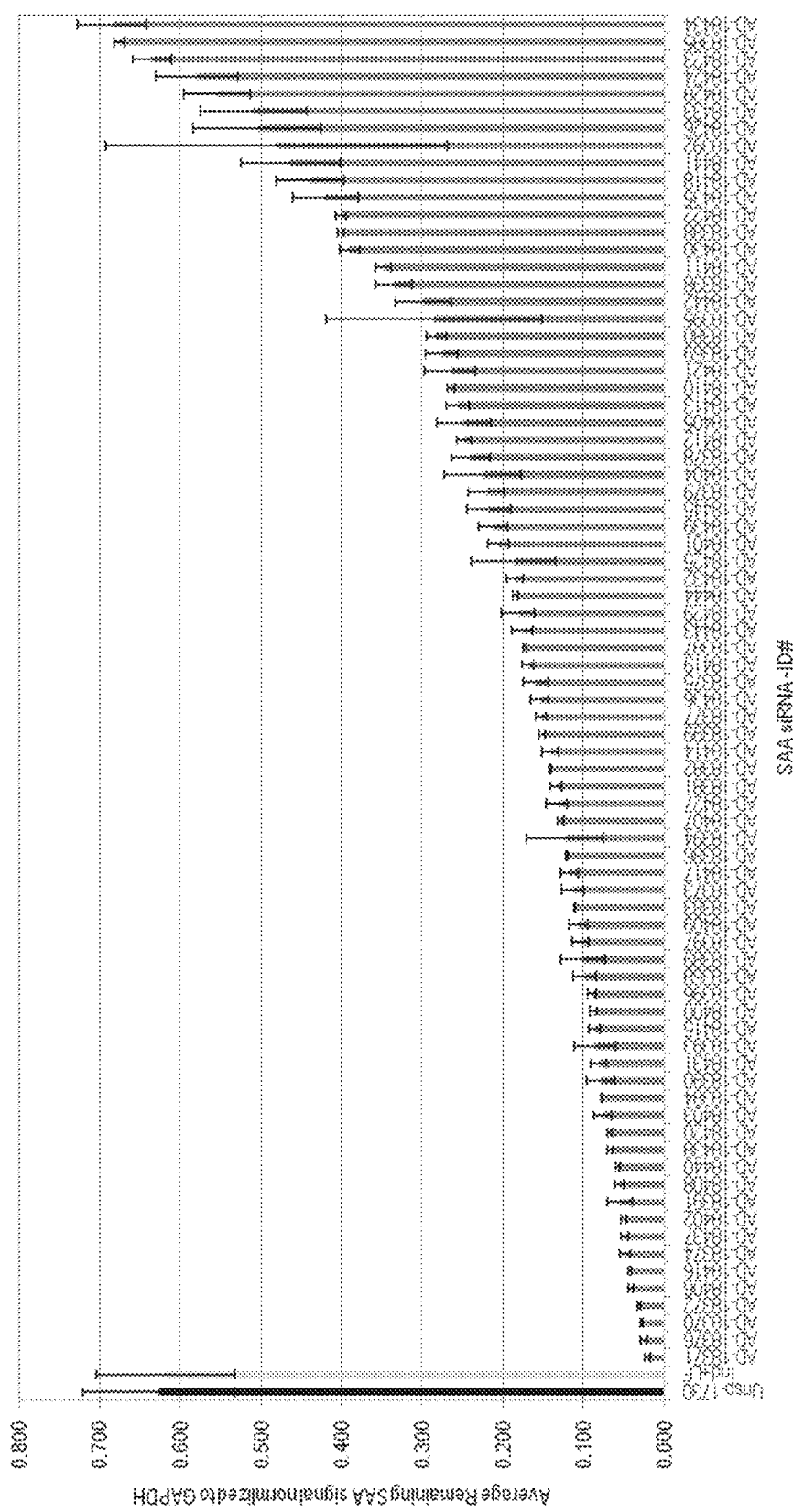
FIG. 2 is a bar graph illustrating SAA mRNA levels in Hep3B cells following administration of candidate SAA siRNAs.
Figure 3:
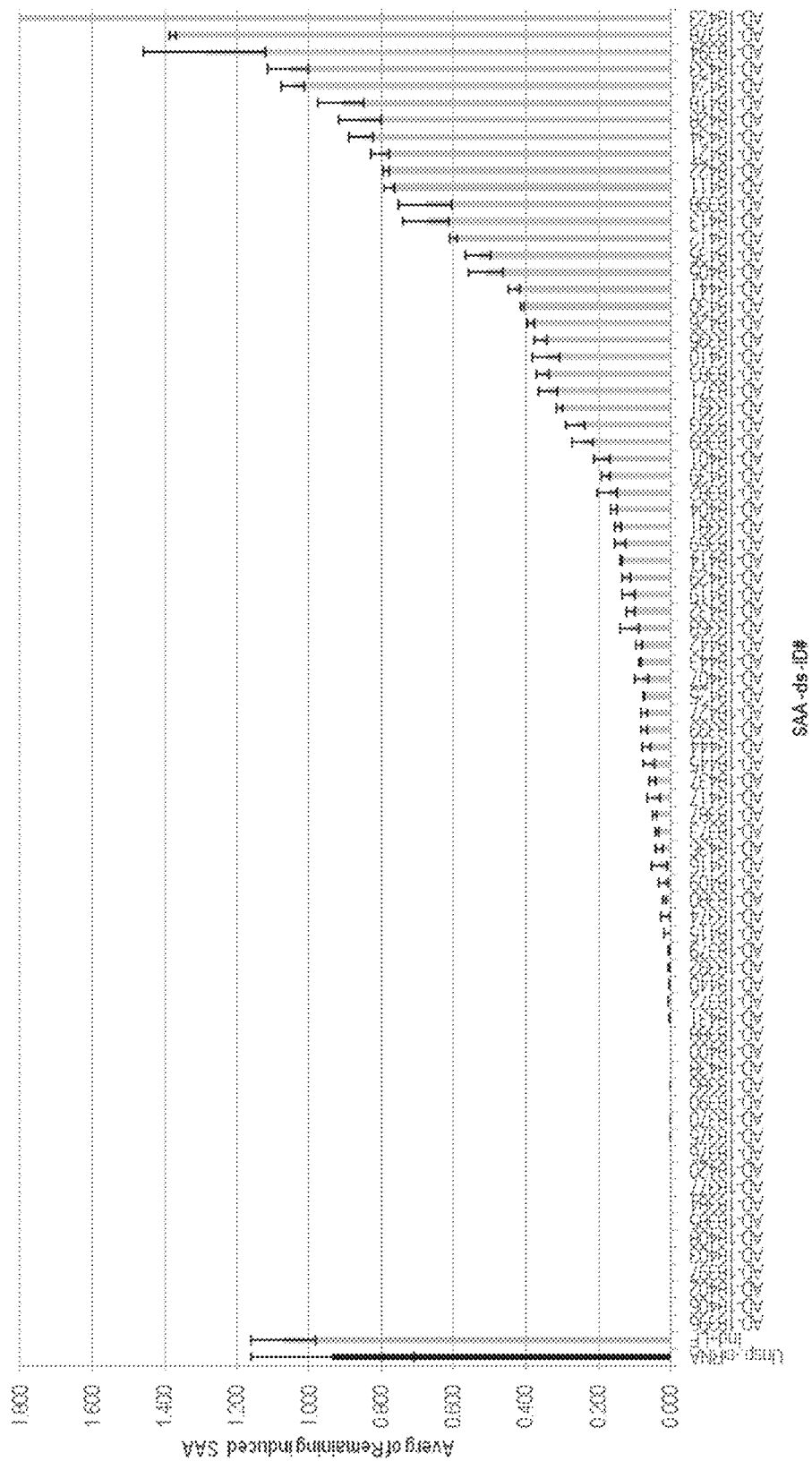
FIG. 3 is a bar graph illustrating SAA protein levels in Hep3B cells following administration of candidate SAA siRNAs.

FIGS. 2 and 3 illustrate SAA mRNA and protein levels in Hep3B cells following administration of the candidate SAA siRNAs as described above. Thirteen of the tested siRNA showed >90% inhibition of mRNA levels, 30 siRNA showed >80% inhibition, and 60 siRNA showed >50% inhibition. More than 30 of the 78 candidate siRNA reduced protein levels by >95%.

Thirty-two of the 78 siRNA were selected for dose response and PBMC cytokine characterization. Selection was based on activity in single dose response experiment and on cross reactivity across species in order to assay duplexes with human only activity, human/cyno activity, human/mouse activity, and human/mouse/cyno activity. Dose response curves for selected siRNAs are shown in FIGS. 4A-4G.

Results of the 1st Round of SAA-siRNAs IC50s an In Vitro Model.

To identify the most potent SAA siRNAs, IC50 of 32 SAA siRNAs were screened in an in vitro model at concentrations ranging from 20 nM to 50 fM (5 fold serial dilutions). SAA-siRNA were reverse transfected in Hep3B using LF-Max. 24 h later, SAA gene expression was induced by adding combined IL-1β and IL6 cytokines. 18 h post-induction, SAA siRNA activity was analyzed by measuring SAA mRNA levels relative to a nonspecific control (BLOCK-IT) using bDNA 2.0. The results of the first round screen are shown in Table 4 below.

TABLE 4

Results of first round screen of SAA siRNAs in in vitro model

| ID# | SAA-siRNA specific/ cross-reactive | IC50 (nM) bDNA |
|---|---|---|
| 18402 | Human | 0.0003 |
| 18384 | Human | 0.0035 |
| 18403 | Human | 0.0052 |
| 18406 | Human | 0.0058 |
| 18386 | Human | 0.0064 |
| 18376 | Human | 0.0301 |
| 18396 | Human | 0.0304 |
| 18372 | Human | 0.0547 |
| 18437 | Human | 0.0687 |
| 18438 | Human | 0.0828 |
| 18408 | Human | 0.0925 |
| 18390 | Human | 0.1490 |
| 18370 | Human | 0.1697 |
| 18416 | Human | 0.2548 |
| 18440 | Human | 0.7700 |
| 18409 | Human | 0.8412 |
| 18400 | Human and cyno | 0.0004 |
| 18431 | Human and cyno | 0.0151 |
| 18397 | Human and cyno | 0.1558 |
| 18420 | Human and cyno | 0.1612 |
| 18399 | Human and cyno | 0.2097 |
| 18415 | Human and cyno | 0.4249 |
| 18374 | Human and cyno | 0.5581 |
| 18425 | Human and cyno | 1.3838 |
| 18414 | Human and cyno | 1.7319 |
| 18436 | Human and cyno | 4.2058 |
| 18379 | Human and mouse | 0.0466 |
| 18373 | Human and mouse | 0.2614 |
| 18417 | Human and mouse | 0.6534 |

Results of the 2nd Round of SAA-siRNA IC50s in an In Vitro Model.

To identify potent SAA siRNAs, IC50 of 32 SAA siRNAs were screened in an in vitro model at concentrations ranging from 20 nM to 50 fM (5 fold serial dilutions). SAA-siRNA was reverse transfected in Hep3B using LF-Max. 24 h later, SAA was induced by adding combined IL-1β and IL6 cytokines. 18 h post-induction, SAA siRNA activity was analyzed by measuring the mRNA level of SAA relative to a nonspecific control (AD-1955) using bDNA 2.0. The results of the second round screening are shown below in Table 5. The shaded siRNAs in Table 5 were selected for further analysis in serum stability assays, in in vivo efficacy studies in mice, and for off-target effects. Selection was based on the best IC50 in each class of cross-reactivities; human/cyno was weighted heavier as it was the likeliest to produce a lead molecule, as molecules in this class had great IC50 and would allow preclinical testing in NHP.

TABLE 5

Results of second round screen of SAA siRNAs in in vitro model

| ID# | SAA-siRNA specific/ cross-reactive | IC50 (nM) bDNA 2nd R | IC50 (nM) TaqMan | IC50 (nM) ELISA |
|---|---|---|---|---|
| 18386 | Human | 0.0001 | 0.0003 | 0.0001 |
| 18402 | Human | 0.0005 | 0.001 | 0.0001 |
| 18406 | Human | 0.0019 | 0.0035 | 0.0007 |
| 18384 | Human | 0.0017 | 0.005 | 0.0017 |
| 18403 | Human | 0.0159 | 0.1737 | 0.0296 |
| 18431 | Human and cyno | 0.0016 | 0.003 | 0.0001 |
| 18415 | Human and cyno | 0.0126 | 0.009 | 0.0018 |
| 18420 | Human and cyno | 0.0097 | 0.0121 | 0.0082 |
| 18397 | Human and cyno | 0.2216 | 0.0377 | 0.0176 |
| 18400 | Human and cyno | 0.5644 | 0.0687 | 0.237 |
| 18374 | Human and cyno | 0.4711 | 0.113 | 0.336 |
| 18399 | Human and cyno | 0.8078 | 0.3986 | 0.606 |
| 18443 | Human and cyno | 3.4945 | 0.9039 | 2.227 |
| 18379 | Human and mouse | 0.0463 | 0.0116 | 0.068 |
| 18373 | Human and mouse | 0.2572 | 0.0555 | 0.078 |
| 18417 | Human and mouse | 0.3150 | 0.1694 | 0.441 |
| 18445 | Human, cyno and mouse | 0.2138 | 0.031 | 0.1499 |
| 18444 | Human, cyno and mouse | 1.2722 | 3.1406 | 1.545 |

Example 4: In Vivo Mouse Model for Testing SAA siRNAs

An in vivo mouse model for testing SAA siRNAs was established. Mice (n=5) were injected intraperitoneally (i.p.) with lipopolysaccharide (LPS) at a concentration of 50 ug on day 0. Mice were bled on day −3 and day 1 following LPS injection and relative mouse SAA OD levels were measured.

FIG. 5 shows that SAA levels were increased in all mice tested 24 hours after LPS injection compared to pre-LPS injection SAA levels. Similar SAA upregulation was achieved with bug of LPS injected i.p. (data not shown).

To test whether SAA siRNA can downregulate SAA levels in vivo, mice were administered siRNA i.v. 6 hours after LPS injection (10 ug i.p.). The siRNAs tested were LNP01 formulated 18445 (10 mg/kg), LNP01 formulated 18379 (10 mg/kg), and SNALP formulated 18445 (2 mg/kg). Controls included PBS and LNP01 formulated 1955 control siRNA (10 mg/kg). Mice were bled 24 hours after siRNA administration and SAA levels were measured using ELISA assay.

SNALP formulation was as follows: DLinDMA/DPPC/Cholesterol/PEG-cDMA (57.1/7.1/34.4/1.4) with a lipid:siRNA of ~7:1.

LNP01 formulation was as follows: ND98/Cholesterol/PEG-Ceramide C16 with a 42:48:10 molar ratio.

Figure 6:
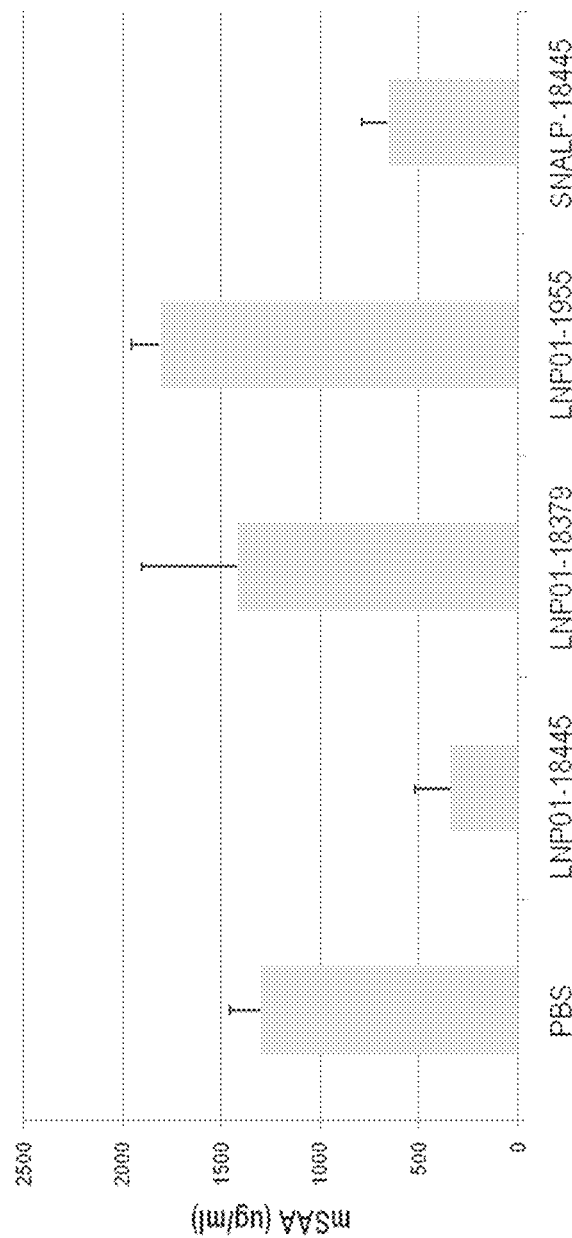
FIG. 6 is a graph showing that LNP01-formulated 18445 and SNALP-formulated 18445 significantly downregulated SAA levels compared to controls.

FIG. 6 shows that LNP01-18445 and SNALP-18445 significantly downregulated SAA levels compared to controls.

As described in Table 2, the sequences of each strand of 18445 are as follows:

| AD-ID # | Strand | Target* | Sequence without Modifications (5'-3') | SEQ ID NO: | Sequence with Modifications (5'-3') | SEQ ID NO: |
|---|---|---|---|---|---|---|
| 18445 | S | 373 | AGACAAAUACUUCCAUGCU | 311 | AGAcAAAuAcuuccAuGcudTdT | 155 |
|  | AS | 391 | AGCAUGGAAGUAUUUGUCU | 312 | AGcAUGGAAGuAUUUGUCUdTdT | 156 |

Alternative dsRNA are included in the invention, e.g., comprising at least 15 nucleotides of the following sense or antisense strands:

| Strand | Sequence (5'-3') | SEQ ID NO: |
|---|---|---|
| S | AGACAAAUACUUCCAUGCUNN | 313 |
| AS | AGCAUGGAAGUAUUUGUCUNN | 314 |
| S | AGAcAAAuAcuuccAuGcu | 315 |
| AS | AGcAUGGAAGuAUUUGUCU | 316 |
| S | AGAcAAAuAcuuccAuGcudTsdT | 317 |
| AS | AGcAUGGAAGuAUUUGUCUdTsdT | 318 |

Example 5. Animal Models for Testing SAA siRNAs

Endogenous mouse models are not suitable for testing human SAA silencing. Therefore, SAA siRNAs can be tested in mice expressing human SAA1 or SAA2 from a plasmid and/or from adenovirus.

Figure 7:
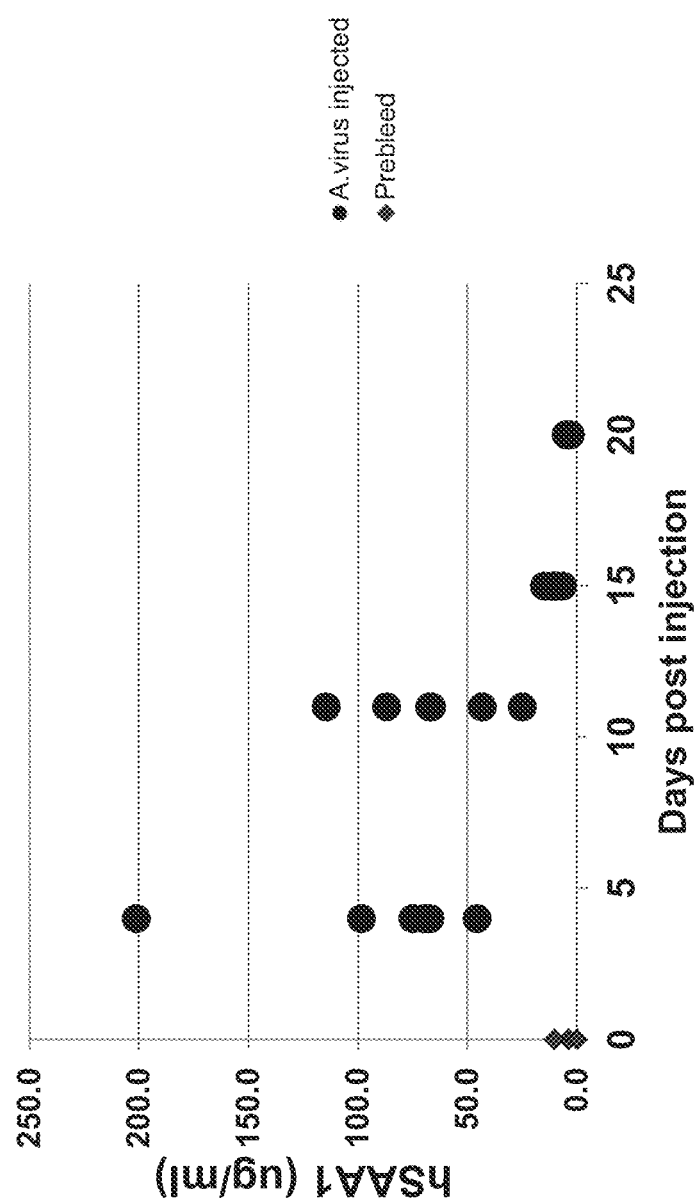
FIG. 7 is a graph showing that expression of hSAA1 can last for approximately 2 weeks after a single injection of hSAA1-adenovirus.

An adenovirus expressing hSAA1 was engineered with a CMV immediate early promoter and enhancer to drive expression of hSAA1 (Hosai et al., JLR 1999). Mice were pre-bled and then administered 4-12×10$^9$ pfu/mouse. Mice were then bled on days 4, 8, 11, 15, and 22 following the virus administration on day 0. FIG. 7 shows that expression of hSAA1 can last for approximately 2 weeks after a single injection of virus.

Figure 8:
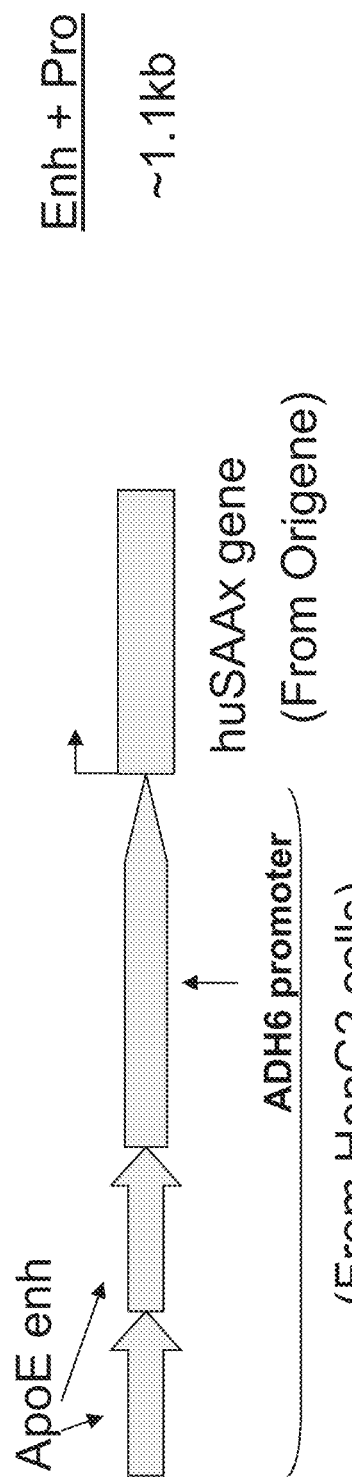
FIG. 8 is a picture showing a construct for expression of hSAA1 in hepatocytes.
Figure 9:
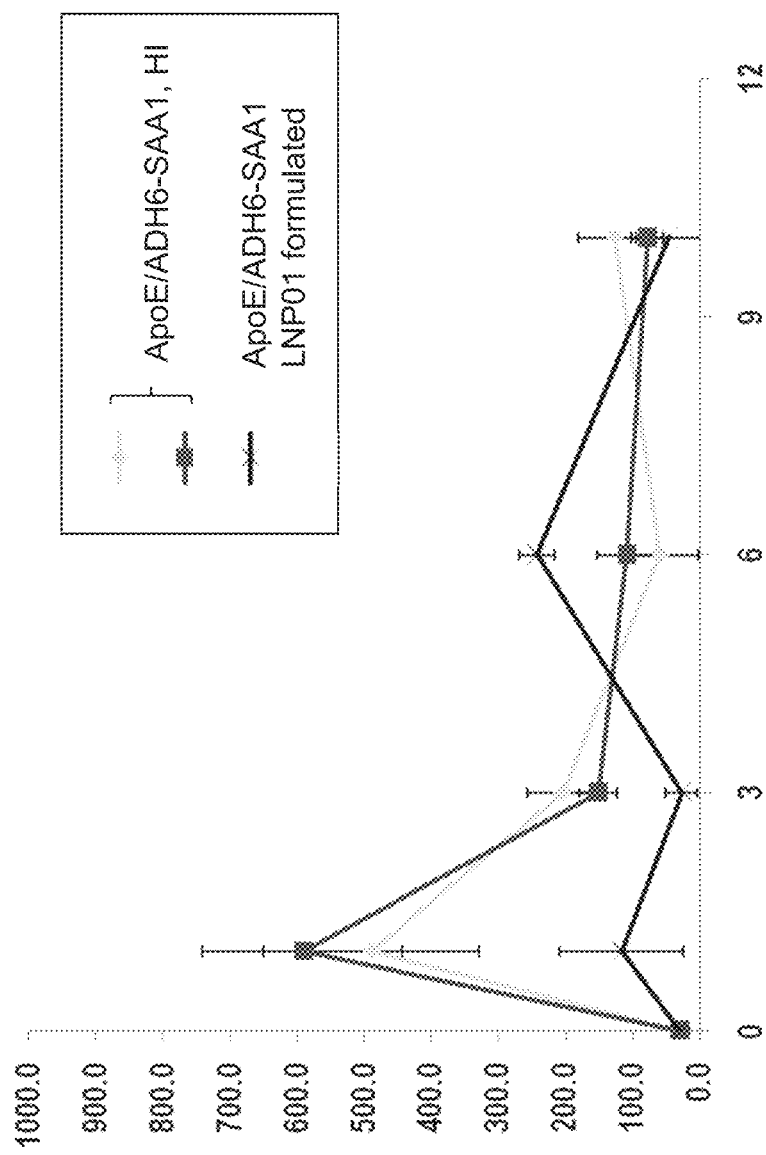
FIG. 9 is a graph showing the expression of hSAA1 in mice following hydrodynamic injection.
Figure 10:
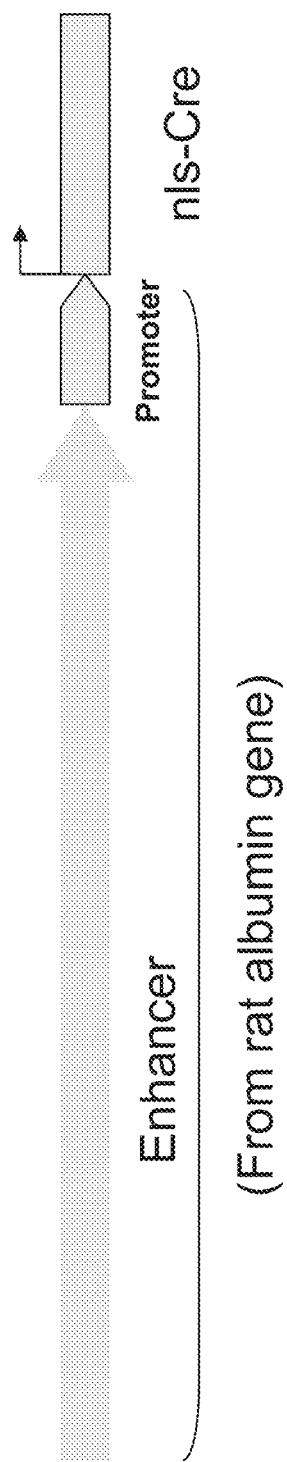
FIG. 10 is a picture showing a construct that was designed for hSAA1 transgene expression.

Hydrodynamic injection was also be used to express human SAA genes in mice (Nguyen et al., J. Surg. Res., 148:1, July 2008, p. 60-66; and Herweijer et al., J. Gene Med., 3:3, 2001, p. 280-291). A construct was designed for hepatocyte-specific hSAA1 expression in mice (FIG. 8). Mice (n=3) were injected via tail vein with 50 ug of the construct plasmid in approximately 2 ml of saline solution in approximately 10 seconds. The expression of hSAA1 in mice following hydrodynamic injection is shown in FIG. 9.

siRNAs can also be tested in mice expressing human SAA1 or SAA2 from a transgene. Transgenic mice can express the human SAA gene constitutively and for a longer period of time. A construct that was designed for hSAA1 transgene expression is shown in FIG. 10 (Postic and Magnuson, Genesis, 2000 Feb.; 26(2):149-150.).

siRNAs can be tested in non-human primate (NHP) models using endogenous SAA expression. Reagents to detect NHP SAA mRNA and protein levels are validated, and then levels of circulating SAA in resting and disease states are determined before administering the candidate siRNAs.

Example 6. Inhibition of SAA Expression in Humans

A human subject is treated with a dsRNA targeted to a SAA gene to inhibit expression of the SAA gene for an extended period of time following a single dose to treat a condition.

A subject in need of treatment is selected or identified. The subject can have AA amyloidosis, rheumatoid arthritis, a neoplasm, psoriatic arthritis, chronic juvenile arthritis, ankylosing spondylitis, Behcet's syndrome, Reiter's syndrome, adult Still's disease, inflammatory bowel disease, hereditary periodic fevers, tuberculosis, osteomyelitis, bronchiectasis, leprosy, pyelonephritis, decubitus ulcers, Whipple's disease, acne conglobata, common variable immunodeficiency hypo/agammaglobulinemia, cystic fibrosis, hepatoma, renal carcinoma, Castleman's disease, Hodgkin's disease, adult hairy cell leukemia, Waldenstrom's disease, a neoplasm, a chronic infections, a chronic inflammatory disease, chronic arthritis, chronic sepsis, a periodic fever syndrome, familial Mediterranean fever, or Crohn's disease.

The identification of the subject can occur in a clinical setting, or elsewhere, e.g., in the subject's home through the subject's own use of a self-testing kit.

At time zero, a suitable first dose of an anti-SAA siRNA is subcutaneously administered to the subject. The dsRNA is formulated as described herein. After a period of time following the first dose, e.g., 7 days, 14 days, and 21 days, the subject's condition is evaluated, e.g., by measuring temperature or one or more inflammation biomarkers. This measurement can be accompanied by a measurement of SAA expression in said subject, and/or the products of the successful siRNA-targeting of SAA mRNA. Other relevant criteria can also be measured. The number and strength of doses are adjusted according to the subject's needs.

After treatment, the subject's temperature and/or inflammation biomarker(s) are lowered relative to the levels existing prior to the treatment, or relative to the levels measured in a similarly afflicted but untreated subject.

Other embodiments are in the claims.

We claim:

1. A double-stranded ribonucleic acid (dsRNA), wherein said dsRNA comprises a sense strand and an antisense strand, wherein each strand is 15-30 nucleotides in length, and wherein the antisense strand comprises a region of complementarity which is complementary to an mRNA encoding Serum amyloid A (SAA) and is complementarity to at least 15 contiguous nucleotides of SEQ ID NO:283.

2. The dsRNA of claim 1, wherein the sense strand consists of the nucleotide sequence of SEQ ID NO:283 and the antisense strand consists of SEQ ID NO:284.

3. The dsRNA of claim 1, wherein the sense strand consists of SEQ ID NO:127 and the antisense strand consists of SEQ ID NO:128.

4. The dsRNA of claim 1, comprising at least one modified nucleotide.

5. The dsRNA of claim 1, comprising at least one modified nucleotide selected from the group consisting of: a 2'-O-methyl modified nucleotide, a nucleotide comprising a 5'-phosphorothioate group, a terminal nucleotide linked to a cholesteryl derivative or dodecanoic acid bisdecylamide group, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a 2'-O-methylcytidine-5'-phosphate, a 2'-O-methyluridine-5'-phosphate, and a non-natural base comprising nucleotide.

6. The dsRNA of claim 1, wherein each strand is 21 nucleotides in length.

7. The dsRNA of claim 1, comprising a dTdT overhang on the 3' end of each strand.

8. The dsRNA of claim 1, wherein the region of complementarity is 19-21 nucleotides in length.

9. The dsRNA of claim 1, wherein the dsRNA is conjugated to a ligand.

10. The dsRNA of claim 1, wherein the dsRNA is formulated in a lipid formulation.

11. The dsRNA of claim 1, wherein upon administration of the dsRNA, the SAA gene is suppressed by at least 60%.

12. The dsRNA of claim 1, wherein the dsRNA has an IC50 of less than 10 pM as measured by branched DNA assay.

13. A cell comprising the dsRNA of claim 1.

14. A vector comprising a nucleotide sequence encoding at least one strand of the dsRNA of claim 1.

15. A cell comprising the vector of claim 14.

16. A pharmaceutical composition for inhibiting expression of an SAA gene comprising the dsRNA of claim 1.

17. A method of inhibiting SAA expression in a cell, the method comprising:

(a) introducing into the cell the dsRNA of claim 1; and (b) maintaining the cell produced in step (a) for a time sufficient to obtain degradation of the mRNA transcript of an SAA gene, thereby inhibiting expression of the SAA gene in the cell.

* * * * *